(12) United States Patent
Loudermilk et al.

(10) Patent No.: US 11,730,458 B2
(45) Date of Patent: *Aug. 22, 2023

(54) SYSTEMS AND METHODS FOR FLUID SAMPLE COLLECTION AND TESTING

(71) Applicant: Marshall Venture Partners LLC, Marshall, TX (US)

(72) Inventors: Alan R Loudermilk, Marshall, TX (US); Herbert Hunt Allred, Dallas, TX (US); Kevin Fuller, Chaska, MN (US); Wayde J Altendorf, Hickson, ND (US)

(73) Assignee: MARSHALL VENTURE PARTNERS LLC, Marshall, TX (US)

( * ) Notice: Subject to any disclaimer, the term of this patent is extended or adjusted under 35 U.S.C. 154(b) by 279 days.

This patent is subject to a terminal disclaimer.

(21) Appl. No.: 16/833,386

(22) Filed: Mar. 27, 2020

(65) Prior Publication Data

US 2020/0383664 A1  Dec. 10, 2020

Related U.S. Application Data

(63) Continuation-in-part of application No. 16/792,175, filed on Feb. 14, 2020.

(60) Provisional application No. 62/970,663, filed on Feb. 5, 2020, provisional application No. 62/805,879, filed on Feb. 14, 2019.

(51) Int. Cl.
*B01L 3/00* (2006.01)
*G01N 1/28* (2006.01)
*A61B 10/00* (2006.01)
*G01N 1/00* (2006.01)

(52) U.S. Cl.
CPC ...... *A61B 10/0096* (2013.01); *A61B 10/0051* (2013.01); *B01L 3/5029* (2013.01); *G01N 1/28* (2013.01); *A61B 2010/0006* (2013.01); *B01L 2400/065* (2013.01); *G01N 2001/002* (2013.01)

(58) Field of Classification Search
CPC ............ A61B 10/0096; A61B 10/0051; A61B 2010/0006; B01L 3/5029; B01L 2400/065; B01L 2200/0689; B01L 2300/0825; B01L 2400/0478; G01N 1/28; G01N 2001/002; G01N 2001/149
See application file for complete search history.

(56) References Cited

U.S. PATENT DOCUMENTS

| 5,244,815 A | 9/1993 | Guirguis |
| 6,277,646 B1 | 8/2001 | Guirguis |
| 6,352,863 B1 | 3/2002 | Guirguis |

(Continued)

FOREIGN PATENT DOCUMENTS

CN  108414512 A  *  8/2018  ......... A61B 10/0051

*Primary Examiner* — Matthew D Krcha
*Assistant Examiner* — Sophia Y Lyle
(74) *Attorney, Agent, or Firm* — Loudermilk + Associates

(57) ABSTRACT

A fluid sample testing apparatus has a fluid collector tube and a fluid collector in fluid communication with a sample holding container. The fluid collector is inserted into and penetrates the fluid collector tube and pressure is generated to release fluid from the fluid collector into the sample holding container, and air passes outside of the apparatus from the fluid collector tube via a vent path. The vent path is sealed with the fluid collector is fully inserted into the fluid collector tube. Indicator or test strips are optionally included in a stem of the fluid collector.

16 Claims, 20 Drawing Sheets

(56) References Cited

U.S. PATENT DOCUMENTS

| | | | |
|---|---|---|---|
| 6,489,172 B1* | 12/2002 | Bachand | A61B 10/0051 |
| | | | 600/572 |
| 7,060,505 B2 | 6/2006 | Guirguis | |
| 7,741,103 B2 | 6/2010 | Guirguis | |
| 7,879,623 B2 | 2/2011 | Guirguis | |
| 7,927,562 B2 | 4/2011 | Wan | |
| 8,940,527 B2 | 1/2015 | Guirguis | |
| 9,198,641 B2 | 12/2015 | Slowey | |
| 9,414,813 B2 | 8/2016 | Engel | |
| 9,462,998 B2 | 10/2016 | Engel | |
| 10,035,146 B2 | 7/2018 | Fuller | |
| 10,076,314 B2 | 9/2018 | Engel | |
| 10,564,155 B2 | 2/2020 | Guirguis | |
| 10,744,507 B2 | 8/2020 | Fuller | |
| 2006/0057027 A1* | 3/2006 | Hudak | A61B 10/0051 |
| | | | 422/549 |
| 2007/0239069 A1* | 10/2007 | Guirguis | G01N 33/5302 |
| | | | 600/584 |
| 2012/0094303 A1* | 4/2012 | Engel | G01N 33/558 |
| | | | 435/7.1 |
| 2014/0017147 A1* | 1/2014 | Kim | B01L 3/50825 |
| | | | 422/501 |
| 2014/0150539 A1* | 6/2014 | Wan | A61B 10/0096 |
| | | | 73/64.56 |
| 2015/0276780 A1* | 10/2015 | Bremer | B01D 53/02 |
| | | | 73/23.41 |

* cited by examiner

SYSTEMS AND METHODS FOR FLUID SAMPLE COLLECTION AND TESTING

CROSS-REFERENCE TO RELATED APPLICATIONS

This application claims priority to Provisional App. No. 62/805,879 filed Feb. 14, 2019 and Provisional App. No. 62/970,663 filed Feb. 5, 2020, and application Ser. No. 16/792,175 filed Feb. 14, 2020 (all of which include common Applicants/inventors hereof), which are hereby incorporated by reference.

FIELD OF THE INVENTION

The present invention relates to substance collection and testing particularly fluid samples, and more particularly the present invention relates to a device that tests a fluid sample for the presence or absence of at least one analyte with improved fluid and air flow characteristics, preferably (but optionally) securing a separate fluid sample for later confirmation, and preferably (but optionally) providing positive identification of an individual associated with the sample. The "dual swab" embodiments referenced therein and herein are sometimes referred to herein as a "Dual Swab Device." Embodiments thereof having only a "single swab" are referred to herein as a "Single Swab Device." Both Dual Swab Devices and Single Swab Devices are within the scope of the present invention and preferably include lateral flow assay strips in a test strip chamber, and preferably may have dual or single test strip cassettes in the test strip chamber as herein after described.

BACKGROUND OF THE INVENTION

Reference is made to co-pending U.S. application Ser. Nos. 15/417,905 and 15/418,044, which are hereby incorporated by reference ("Referenced Patent Documents") (but see in particular FIGS. 19-25 of the '044 application and related description, and the '905 application in its entirety).

Drug and other analyte testing has become ubiquitous in modern society. In homes, doctors' offices, law enforcement vehicles and offices, athletic facilities, and the workplace, effective, inexpensive and reliable testing devices have been sought. There is also a growing need for devices to test bodily fluids for substances that may assist in the diagnosis or management of diseases and other medical conditions.

The marketplace responded and is now replete with many devices directed to the testing of blood, urine or saliva. However, these devices may require a series of tests involving the shifting of the fluid sample being tested to different containers and/or the removal of the fluid sample to distant locations. These devices may also require the test administrator to handle the test subject's bodily fluids, incurring a danger of disease exposure.

Once an initial test result has been obtained, further testing of the same fluid sample to confirm or refine the initial test result is often required. For a membrane test strip device, the fluid sample may not even be retained once the initial result is obtained, necessitating retention of a split sample. The need to retain a split sample incurs the risk that a sample could be lost, mislabeled, or contaminated.

Oftentimes, the chain of custody associated with a test sample imbues the results with doubt, as the fluid sample may become contaminated, misplaced or a different fluid sample may be substituted entirety. In many instances, identification of the test subject associated with the fluid sample is critically dispositive.

Prior art testing devices include those disclosed in U.S. Pat. Nos. 7,879,623 and 8,940,527, both entitled "Integrated Device for Analyte, Testing, Confirmation, and Donor Identity Verification" and both identifying Raouf A. Guirguis as the sole inventor. U.S. Pat. Nos. 7,879,623 and 8,940,527 are both hereby incorporated by reference. The patents disclose an apparatus for fluid sample collection and analyte testing, including a single sample receiving member and at least one membrane test strip, and optionally a sample retention member, fingerprint acquisition pad, and/or fluid collector. It also provides a fluid collection apparatus having an absorbent material, compression element, and closure element, and optionally a lid that allows the apparatus to be used in conjunction with a fluid container. Also provided are methods of collecting, testing, and retaining a fluid sample and verifying the identity of one or more individuals associated with the sample, such as the test subject, test administrator, and/or witnesses. The components for collecting, testing, and retaining a fluid sample are in fluid communication with the other components of the testing device.

There is also a growing need for devices directed to testing for contaminants that may be found in food or water, such as pollutants, allergens, and harmful microbes. In some instances, it may be desirable to retain a fluid sample for confirmation testing or further analysis, retain a split fluid sample of the original sample for confirmation testing or further analysis, or to provide positive identification of the test administrator.

The Department of Transportation's (DOT) rule, 49 C.F.R. Part 40, describes required procedures for conducting workplace drug and alcohol testing for the Federally regulated transportation industry. Within this rule, definitions for split sample and split sample collection are provided. Split specimen is defined as, in drug testing, a part of the urine specimen that is sent to a first laboratory and retained unopened, and which is transported to a second laboratory in the event that the employee requests that it be tested following a verified positive test of the primary specimen or a verified adulterated or substituted test result. Split specimen collection is defined as a collection in which the urine collected is divided into two separate specimen bottles, the primary specimen (Bottle A) and the split specimen (Bottle B).

Thus, a need exists in the industry to combine the simplicity of current membrane test strip technology with the ability to positively identify the test subject and/or the test administrator, as well as the capability to secure a split portion of the fluid sample with a single device for later confirmation, within a single device.

Also, a need exists in the industry for such devices to have reduced "push pressure" for locking the swab or swabs in the device, which facilitates operation by users of varying physical strength. And a need also exists for improved test strip carriers for strip testing substances with a propensity to bind or stick to various surfaces, such a substance being THC.

Also incorporated by reference herein are the disclosures of U.S. Pat. Nos. 9,414,813 and 10,035,146.

SUMMARY OF THE INVENTION

In accordance with certain preferred embodiments of the present invention, a fluid sample testing apparatus has: a housing with a test chamber and a first fluid collector tube of a first diameter and a second fluid collector tube of a second diameter, wherein the test chamber is in fluid communication with the first fluid collector tube; a sample holding container in fluid communication with the second fluid collector tube; and first and second fluid collectors, wherein the first fluid collector is adapted for insertion into the first fluid collector tube and upon insertion into the first fluid collector tube pressure is generated to release fluid from the first fluid collector into the test chamber via an opening between the test chamber and the first fluid collector tube, wherein air passes outside of the apparatus from the test chamber via an opening from the test chamber into the first fluid collector tube, and wherein the second fluid collector is adapted for insertion into the second fluid collector tube concurrently with insertion of the first fluid collector into the first fluid collector tube and upon insertion into the second fluid collector tube pressure is generated to release fluid from the second fluid collector into the sample holding container, wherein air passes outside of the apparatus from the second fluid collector tube.

The apparatus may have the first fluid collector having an upper sealing portion such that upon substantially complete insertion into the first fluid collector tube the upper sealing portion seals the opening between the test chamber and the first fluid collector swab tube. The apparatus may have the second fluid collector tube having a shoulder portion in proximity to the sample holding container of a diameter smaller than the second diameter, wherein the second fluid collector has a lower sealing portion such that upon substantially complete insertion into the second fluid collector tube the lower sealing portion seals the sample holding container from an upper portion of the second fluid collector tube. The first and second fluid collectors may comprise individual single swabs coupled together with a locked cap. The second diameter preferably is greater than the first diameter. The test chamber preferably has a top cap connected to the housing that is sealed from outside of the apparatus, preferably in an air and water tight manner such as by sonic welding.

Embodiments of the invention further include a cassette for holding one or a plurality of test strips, wherein the cassette includes one or more channels for holding the one or more test strips and includes at least a first channel for holding a first strip, the first channel having a plurality of projections from each of two opposite side walls of the first channel, wherein the plurality of projections define a center portion in which the first strip is positioned, wherein the plurality of projections position the first strip to reduce or prevent contact between the first strip and the side walls of the first channel, wherein the first channel also has a floor having a plurality of raised portions, wherein the plurality of raised portions position the first strip to reduce or prevent contact between the first strip and the floor of the first channel. Bumps on the front face of the cassette also are provided in certain embodiments, as are side legs that are tapered or have a smaller dimension at a bottom portion compared to a larger dimension at an upper portion.

Embodiments of the present invention also include a fluid sample testing apparatus having a housing with a test chamber and a first fluid collector tube of a first diameter and a second fluid collector tube of a second diameter, wherein the test chamber is in fluid communication with the first fluid collector tube; a sample holding container in fluid communication with the second fluid collector tube; first and second fluid collectors, wherein the first fluid collector is adapted for insertion into the first fluid collector tube and upon insertion into the first fluid collector tube pressure is generated to release fluid from the first fluid collector into the test chamber via an opening between the test chamber and the first fluid collector tube, wherein air passes outside of the apparatus from the test chamber via an opening from the test chamber into the first fluid collector tube, and wherein the second fluid collector is adapted for insertion into the second fluid collector tube concurrently with insertion of the first fluid collector into the first fluid collector tube and upon insertion into the second fluid collector tube pressure is generated to release fluid from the second fluid collector into the sample holding container; and a gasket positioned in the second fluid collector tube having an upper portion for engaging a wall of the second fluid collector tube and a lower portion of smaller diameter than the upper portion for insertion into an opening of the sample holding container, wherein the gasket is positioned at an upper location in the second fluid collector tube upon insertion of the second fluid collector into the second fluid collector tube, wherein the gasket is positioned at a lower location in the second fluid collector tube after insertion of the second fluid collector into the second fluid collector tube and at the lower location the gasket forms a seal with the sample holding container, wherein air passes outside of the apparatus from the second fluid collector tube before the gasket is positioned at the lower location.

The first fluid collector may have an upper sealing portion such that upon substantially complete insertion into the first fluid collector tube the upper sealing portion seals an opening between the test chamber and the first fluid collector swab tube. The apparatus may have the first fluid collector having a lower sealing portion adapted to form a sliding seal between the lower sealing portion and a surface wall of the first fluid collector tube as the first fluid collector is inserted into the first fluid collector tube. The upper sealing portion may be adapted to form a fixed seal for the opening between the test chamber and the first fluid collector tube and have a shape different from the lower sealing portion. The upper sealing portion may form a stopper seal for the opening between the test chamber and the first fluid collector tube, and the lower sealing portion may form a syringe plunger seal between the lower sealing portion and a surface wall of the first fluid collector tube. The lower sealing portion may be formed to have a plurality of spaced apart o-ring portions to form the syringe plunger seal. The lower sealing portion may be formed to have a textured surface to form the syringe plunger seal.

Accordingly, it is an object of the present invention to provide single and dual swab fluid collection and testing devices having improved air venting/air flow characteristics to improve fluid transfer into a test chamber via a channel and optionally into a confirmation vial.

It is another object of the present invention to provide single and dual swab fluid collection and testing devices having improved user experience by having reduced back pressure when swab assemblies are inserted into and pressured downward in a preferably locked position.

It is yet another object of the present invention to provide swab assemblies having a stopper type upper seal and a syringe type lower seal.

It further is an object of the present invention to provide a fluid collection apparatus having a funnel shaped gasket in a first position whereby a swab may be initially compressed, and upon pressure build-up move to a second position whereby the gasket seals to the housing and vial, wherein prior to being in the second position air may vent out of the apparatus.

Finally, it is an object of the present invention to provide a strip holding cassette for use in testing fluid samples having one or more channels with side projections and floor bumps that position a strip so as to reduce or prevent contact of the strip with side walls of the channel or a floor of the channel.

BRIEF DESCRIPTION OF THE DRAWINGS

The above objects and other advantages of the present invention will become more apparent by describing in detail the preferred embodiments of the present invention with reference to the attached drawings in which.

DETAILED DESCRIPTION OF THE PREFERRED EMBODIMENTS

Figure 1:
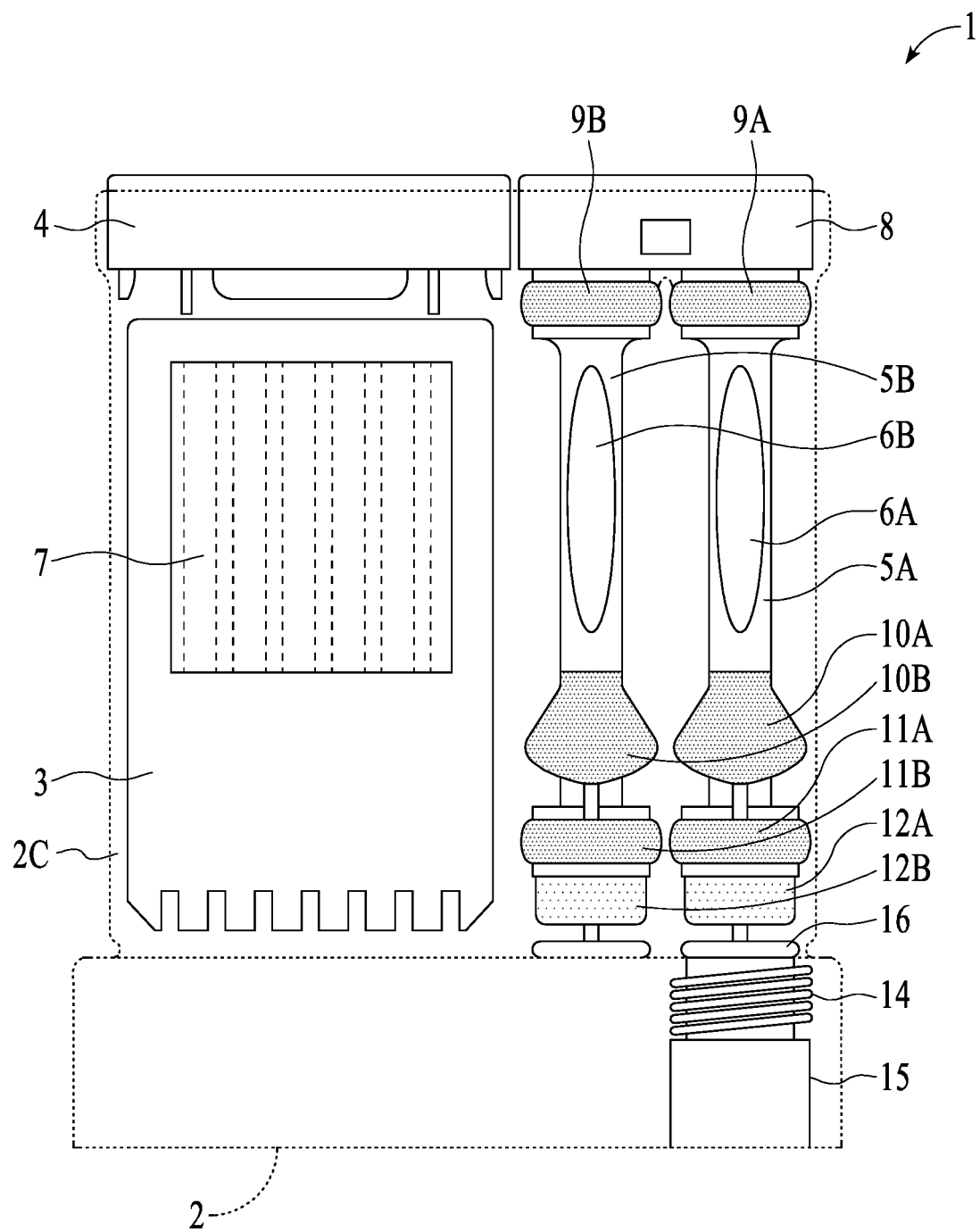
FIGS. 1-3 illustrate overall device views of a fluid sample collection and testing device in accordance with certain preferred embodiments of the present invention.

The present invention will be described in greater detail with reference to certain preferred and alternative embodiments. As described below, refinements and substitutions of the various embodiments are possible based on the principles and teachings herein.

As will be understood from the Referenced Patent Documents, particularly in view of this disclosure, the present invention utilizes a fluid (e.g., saliva) absorption or capture device (herein a "swab" or sponge/sponge-like material that may absorb/contain and release the fluid of interest) that preferably captures oral fluids such as by insertion of the swab into a subject's mouth, whereby oral fluids are captured/absorbed into the swab (where the term "saliva" is used, it is to be understood that other than oral fluids also may be used in accordance with embodiments of the present invention). As an illustrative example, in accordance with alternative embodiments of the present invention, a swab may be wetted with water or other fluid such as alcohol, then brought into contact with a dry, powder or other substance (which may be suspected to be a drug, contaminant or other material of interest or concern), and then swabs inserted into the device for testing. Each swab preferably is mounted on a stem type device so that the absorbent material of the swab/sponge may be readily positioned in the subject's mouth, with the stem holdable much like a lollipop. After a sufficient amount of time, e.g., 2-5 minutes, and preferably as indicated by an indicator implement (hereinafter described), saliva typically is captured in sufficient volume so as to be introduced via a dual swab into the housing of a Dual Swab Device for testing and preferably confirmation (as will be described in more detail hereinafter). In alternative Single Swab Devices, saliva typically is captured in sufficient volume so as to be introduced via a single swab into the housing of a Single Swab Device for testing (as will be described in more detail hereinafter). In both Single and Dual Swab Devices, insertion of the swab via the stem into the housing preferably causes compression of the swab into a bottom portion of a swab tube in the housing, forcing saliva to be released from the swab wherein pressure is generated such that saliva is forced or pushed from the swab tube into a lateral flow assay strip chamber through an opening sized for the particular fluid under examination (there is flow communication via a channel from the swab tube in the housing into strip chamber). The saliva contacts the strips whereby the previous of drugs, diseases or other substances may be detected in desirable levels (see the Referenced Patent Document). In Dual Swab Devices, a second swab tube is provided so that a second swab may be compressed such that saliva is released and captured into a vial, separate from the chamber described above housing the assay strips. Upon full insertion of the dual swabs, the unit is sealed so as to minimize fluid escape from the device. In Dual Swab Devices, a relatively prompt initial screening may be made via the assay strips, and a second sample is captured in the vial, which is separate from, and not in flow communication with, the chamber housing the strips, which may be made available for confirmation testing in a laboratory, such as in a high complexity via for example mass spectroscopy, such as Liquid Chromatography Mass Spectroscopy (LC-MS). In Single Swab Devices, the confirmation vial is not provided, and only the screening via the assay strips preferably is provided.

Figure 2:
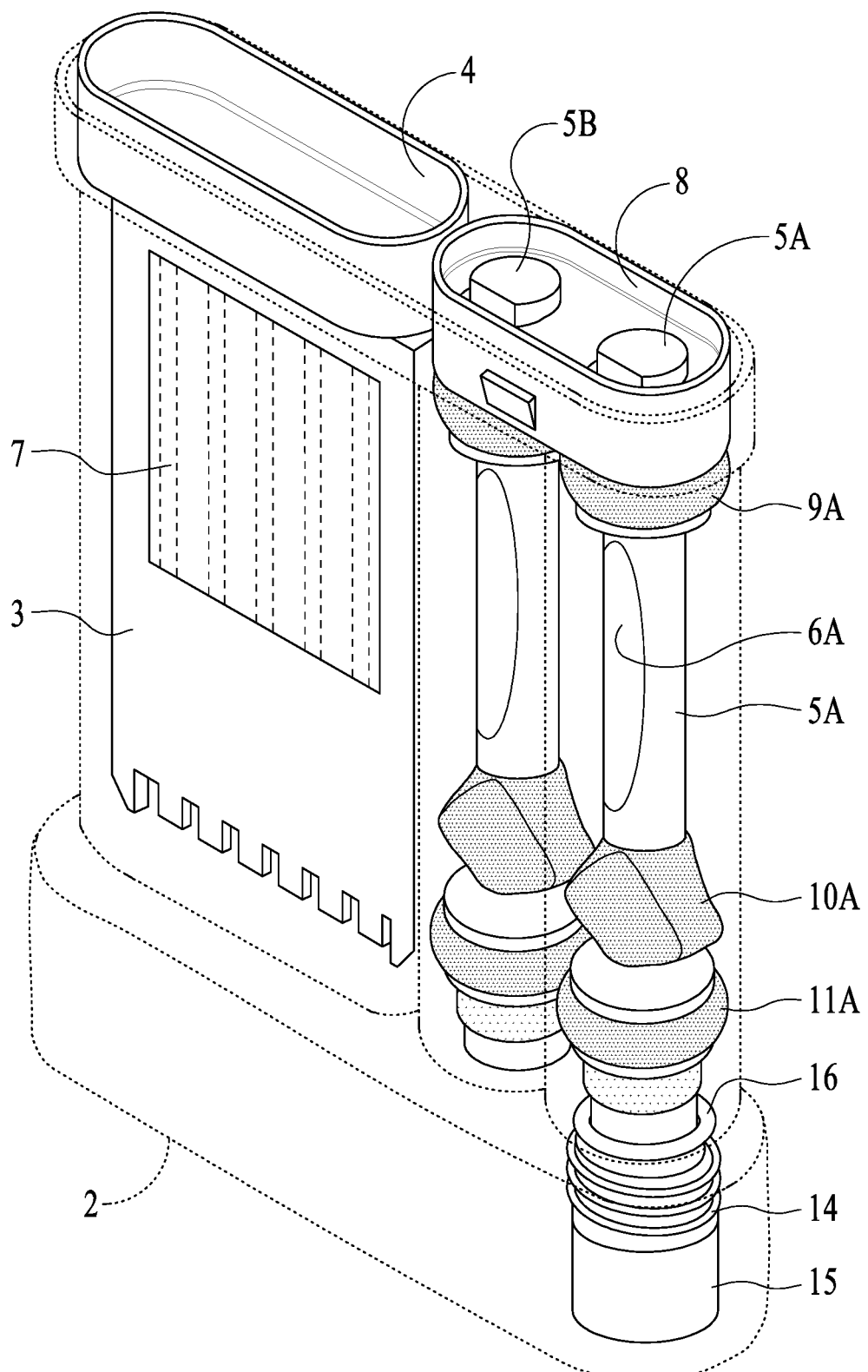

Referring now to FIGS. 1 and 2, an assembled Dual Swab Device 1 is illustrated. Housing 2 (preferably plastic such poly carbonate PC or general purpose polystyrene GPPS or similar materials) provide the main body of the unit. In a test chamber as illustrated, strip card/carrier or cassette 3 is provided, which includes one or a plurality of assay strips generally illustrated as 7. In operation, fluids are introduced into test chamber 2C of housing 2 so that the presence or absence of one or more target analytes (e.g., drugs, disease markers, etc.) may be detected based on the particular characteristics of the one or more strips 7. Test chamber 2C of housing 2 has an upper body plug or top cap 4, which preferably is sonic welding to housing 2 to provide an air and water tight seal, with the sonic welding carried out after cassette 3 has been inserted into test chamber 2C. As illustrated, a Dual Swab Device preferably includes two swab assemblies, connected via a preferably snap together, locking cap or dual stem handle 8 (each swab assembly is inserted into stem handle 8 and each has a locking feature for engaging a corresponding feature in stem handle 8 to lock them together to create a dual swab assembly). Each of swab assemblies 5A and 5B consist generally of the following: stems 6A and 6B (preferably plastics such as described for housing 2) having at least a visual window (indicated by ovals in FIG. 1) such that color changes of an indicator strip inside of stems 6A and 6B may be visible to an observer (and possibly the subject) (indicator strips are described in greater detail hereinafter, and such description is applicable here); preferably soft or elastomeric type material (such as by "second shotting" or "over molding" provide seals 9A and 9B at an upper portion of the swab assemblies, and seals 11A and 11B at a lower portion of the swab assemblies; swabs 12A and 12B (absorbent or sponge like material, such as described elsewhere herein), preferably secured by adhesive or other attachment, are secured to the bottom of stems 6A and 6B and provide the saliva capture for the devices (shown in compressed form in FIG. 1); tooth rests 10A and 10B, preferably of a similar material as seals 9A, 9B, 11A and 11B, are preferably provided so that a comfortable and desired resting place for front teeth of the subject (this enables the swab stem to be more comfortably held in a manner so that swabs 12A and 12B may more optimally capture oral fluids, etc.). Vial 15 is provided in Dual Swab Devices so that a confirmation sample may be obtained. Vial 15 preferably is secured to housing 2 via threads 14 of housing 2 or similar securing mechanism, and preferably sealed with O ring 16. As should be understood based on the description herein, swab assembly 5A may be compressed in tube 2A of housing 2 (see FIG. 3) and release oral fluid into vial 15 via fluid channel 2D (vial 15 is in fluid communication with tube 2A as illustrated), and swab assembly 5B may be compressed in tube 2B of housing 2 and release oral fluid into test chamber 2C via channel 23 (see FIG. 4) (test chamber 2C is in fluid communication with tube 2B via channel 23 as illustrated).

Figure 3:
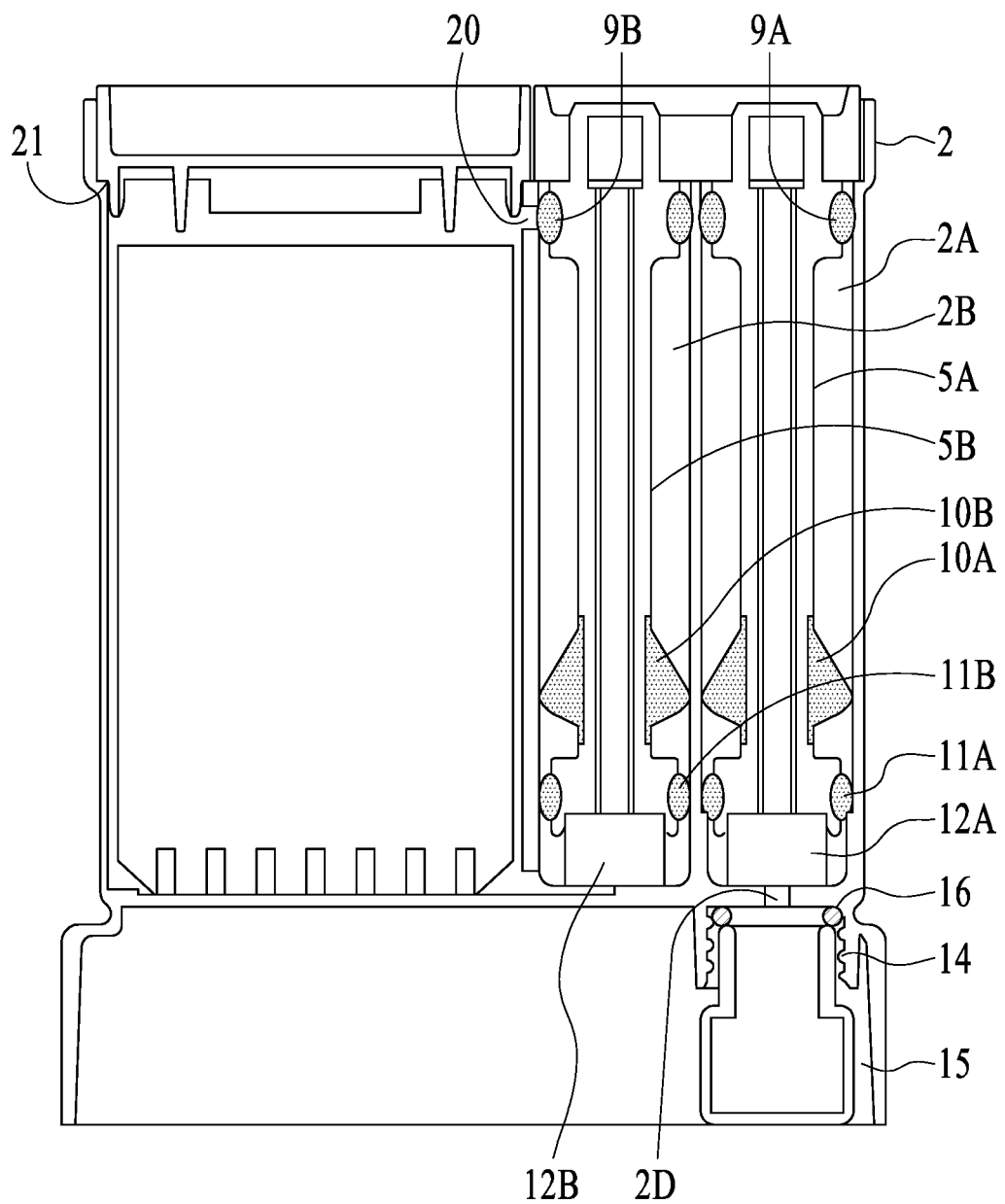
Figure 7:
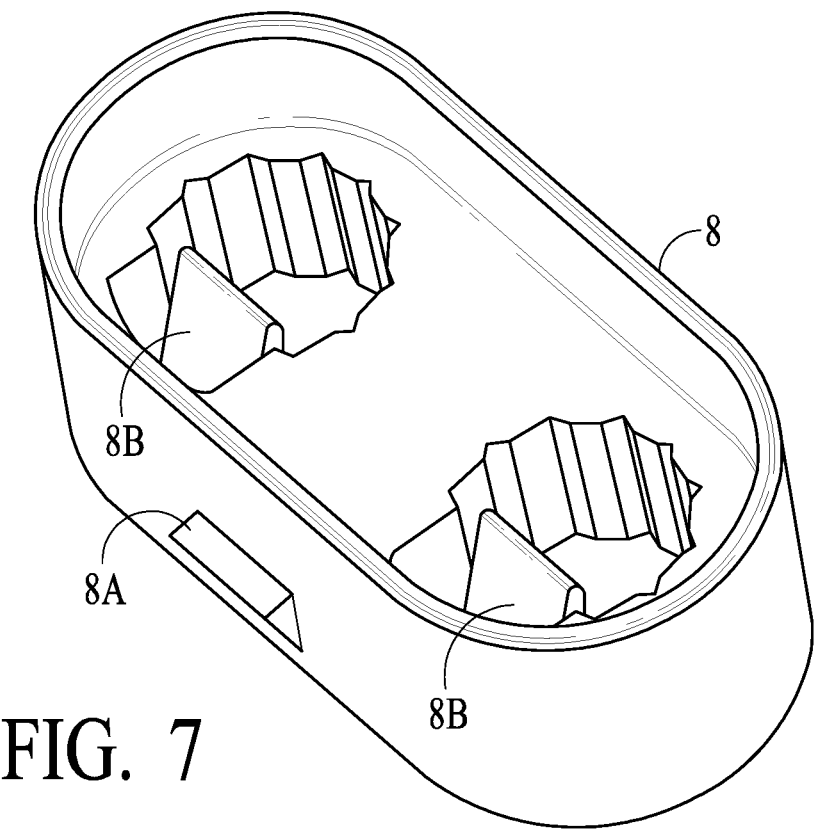
FIG. 7 illustrates a dual swab stem handle for connecting two swab assemblies to make a dual swab assembly in accordance with certain preferred embodiments of the present invention.

FIG. 3 illustrates additional attributes of preferred embodiments of the present invention, in cross section. Focusing now on the left most swab assembly 5B and swab tube 2B of housing 2 (herein sometimes called the "strip swab tube"), strip swab assembly 5B is shown in cross section fully inserted into the strip swab tube (swab 12B is compressed). Swab tube 2B preferably has a diameter of a first dimension, and seal 11B has a dimension such as to form a relatively tight fit/seal with swab tube 2B. As strip swab assembly 5B is inserted into swab tube 2B, the relatively tight fit/seal causes compression of swab 12B (and saliva release from the swab) and results in interior pressure in the lower portion of the swab tube 2B, with the result that saliva is released from swab 12B and forced or pressured moved into test chamber 2C of housing 2 via an opening (see opening or saliva passage 23 of FIG. 4). The size of this opening preferably is determined based on, for example, the particular fluid being tested and its characteristics, such as viscosity. What is important is that the relatively tight fit/seal of swab assembly 5B and the diameters of swab tube 2B and seal 11B are such that a plunger/compressive effect is achieved, and saliva is released and forced via opening/passage 23 into test chamber 2C. As interior pressure in test chamber 2C of housing 2 can increase, in preferred embodiment air is vented from test chamber 2C into test swab tube 2B via a vent opening (see opening/vent 20 of FIG. 3, which provides flow communication for air venting between test chamber 2C and swab tube 2B). Note that there is not a seal present at the top of swab tube 2B while swab assembly 5B is being inserted (stem 6B of swab assembly 5B being less in cross section than the interior dimension of swab tube 2B). Thus, while being inserted, pressure from the compressed swab forces saliva into test chamber 2C, air is vented from test chamber 2C via opening/vent 20 into swab tube 2B where it may escape out the top, thereby reducing "back pressure" experienced by the user pushing swab assemblies 5A and 5B into housing 2. Once swab assembly 5B, however, is fully inserted into swab tube 2B (and preferably locked such as with a locking tab—see FIG. 7 and dual stem handle 8 and locking tab 8A, which will be understood to engage with an indentation or hole of an upper portion of the tube section of housing 2 to provide a locking mechanism), seal 9B seals swab assembly 5B against swab tube 2B AND seals off opening/vent 20. Thus, operationally, opening/vent 20 allows air release during the insertion process (to prevent pressure build-up in the test chamber as saliva is forced in), and then is closed by a preferably overmold seal upon full insertion of the swab tube assembly.

Figure 4:
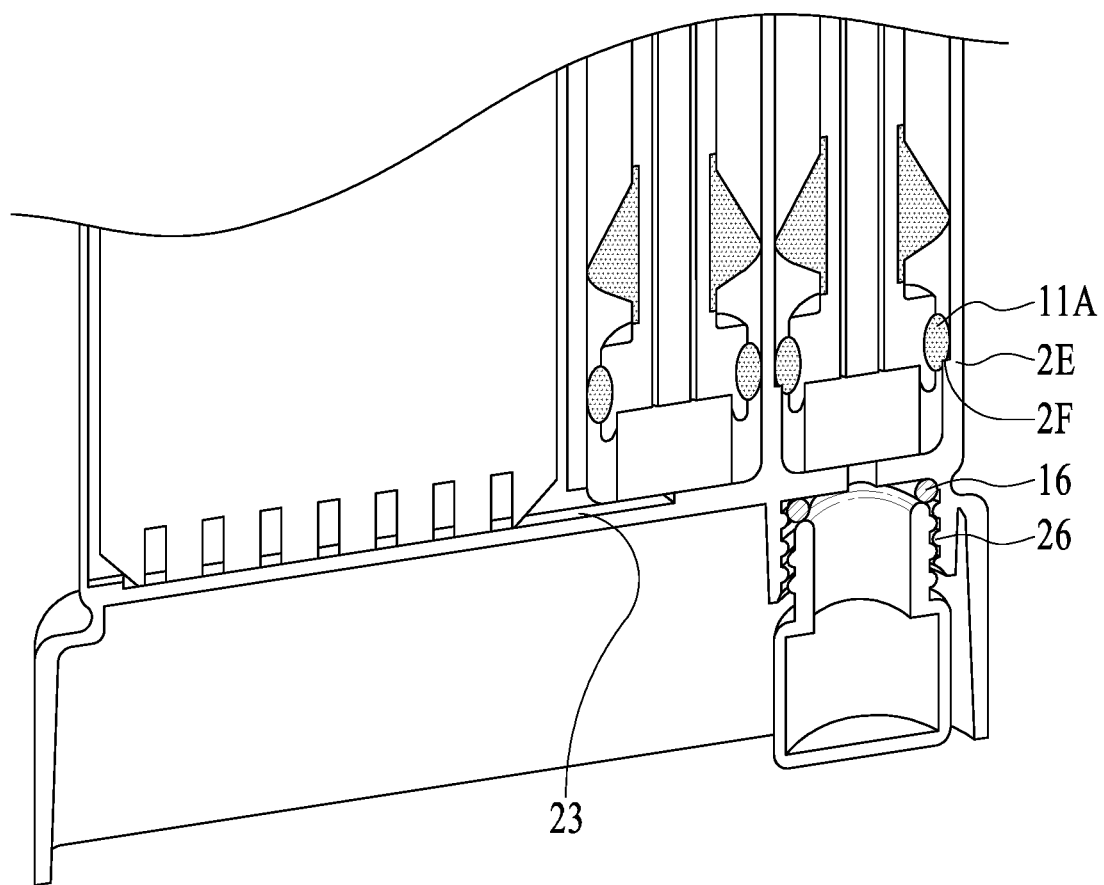
FIG. 4 illustrates fluid communication between a swab tube and a test chamber and between a swab tube and a confirmation vial in accordance with certain preferred embodiments of the present invention.

The right most swab tube 2A of housing 2 (herein sometimes referred to as "confirmation swab tube") operationally receives swab assembly 5A. Swab tube 5A has a second dimension (illustrated as 2E preferably down to a lower extremity as illustrated), and seal 11A has a diameter such as to form a relatively loose fit/seal with swab tube 5A (and is not air tight but substantially water tight). Thus, upon insertion of swab assembly 5A into swab tube 2A, swab 12A is compressed and saliva is released into vial 15 via fluid channel 2D, while air may be vented out via the top of swab tube 2A around lower seal 11A. Swab tube 2A preferably has a shoulder (narrower diameter of a third dimension, less than the second dimension, generally illustrated as 2F) at a lower portion such that seal 11A may tightly engage the shoulder (2F) and seal vial 15 from other portions of the unit upon swab assembly 5A being fully inserted into swab tube 2A (see seal 11A in FIG. 4, showing the engagement of seal 11A with the shoulder (2F) of swab tube 2A). FIG. 4 also illustrates a seal between vial 15 and housing 2 (see o-ring seal 16 of FIG. 4), and securing of vial 15 to housing 2 such as by a thread mechanism (see vial threads 26 of FIG. 4, which engage corresponding threads 14 of housing 2). What is important is that, while swab assemblies 5A and 5B preferably are of the same size, the diameters of swab tube 2B and swab tube 2A are of different dimensions, such that pressure is generated to force saliva into test chamber 2D (with air vented from test chamber 2D via opening/vent 20 to swab tube 2B), and air from confirmation swab tube 2A is vented from the top of confirmation swab tube 2A. In exemplary preferred embodiments, the third dimension is less than the first and second dimensions.

Figure 5A:
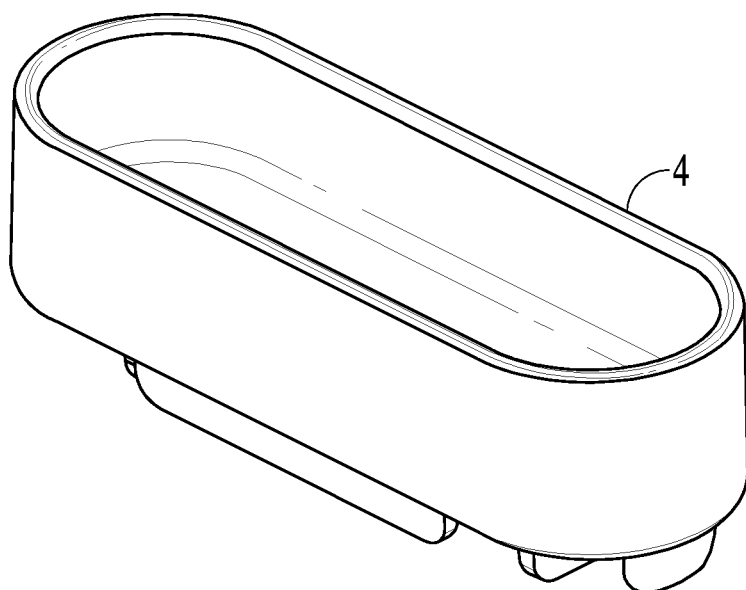
FIGS. 5A and 5B illustrate a top cap preferably sonic weldable in accordance with certain preferred embodiments of the present invention.
Figure 5B:
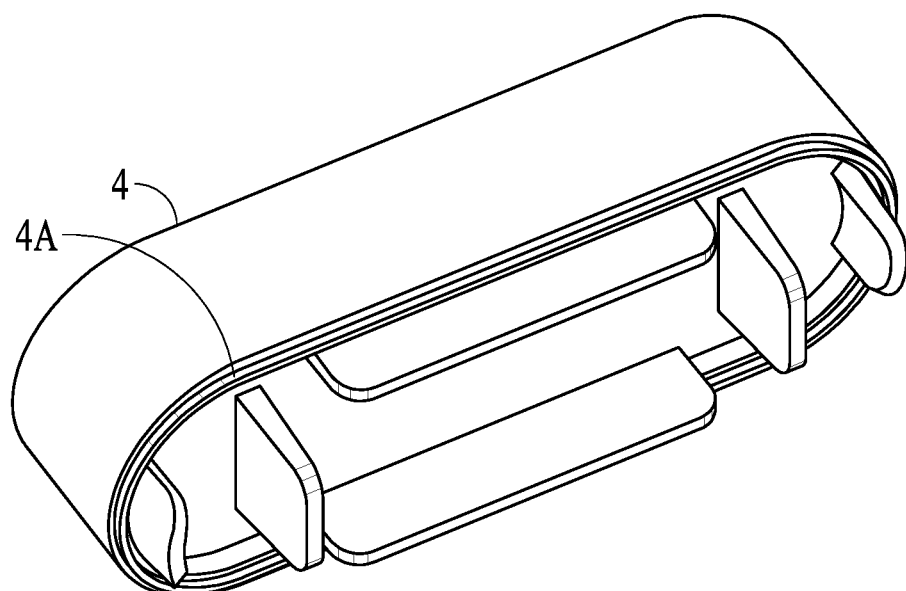

FIGS. 5A and 5B illustrate body top cap 4, which is sealed to the top of the test chamber of housing 2 preferably via sonic weld to create a air and water tight seal. Body top cap 4 preferably has energy director 4A such as to facilitate the sonic weld process.

Figure 6A:
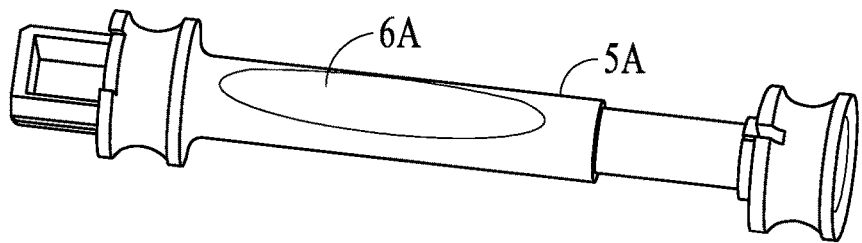
FIGS. 6A-6C illustrate a swab stem and a swab assembly in accordance with certain preferred embodiments of the present invention.
Figure 6B:
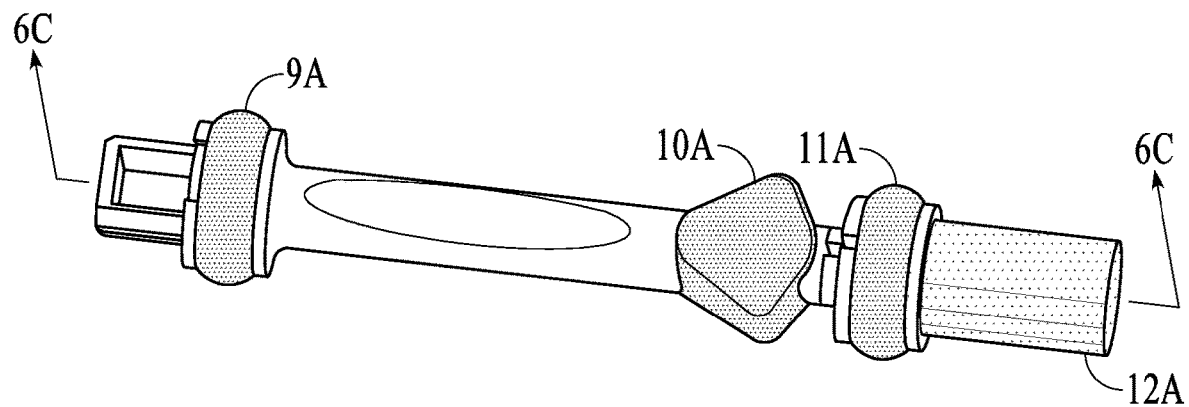
Figure 6C:
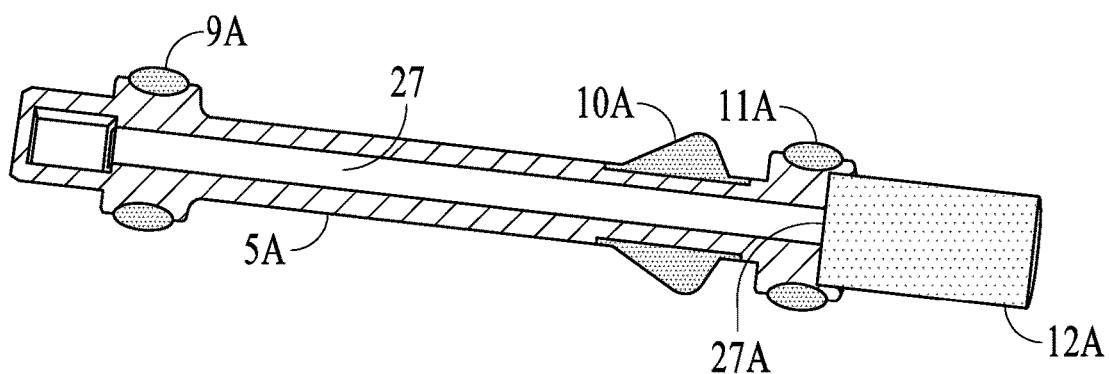

FIGS. 6A-6C illustrate swab assembly 5A is various stages of manufacture. FIG. 6A will be understood to be after the first shot, or first injection molding, of the plastic of swab assembly 5A (stem 6A is illustrated). FIG. 6B will be understood to be after the second shot, or second injection molding of the softer, more compliant material that is used, preferably, for seals 11A and 11B and teeth rests 10A and 10B as described elsewhere herein. FIG. 6C illustrates swab assembly 5A in cross section such that indicator strip 27 is visible. In preferred embodiments, swab assembly 5A (and preferably 5B) has interior portion with an opening (preferably a slit) such that an indicator strip 27 may be positioned to engage with swab 12A at one end (illustrated as contact point 27A), and then extend up stem 6A so as to be visible through the oval window of stem 6A. As will be understood, indicator strip 27 changes color when wet or saturated, and is calibrated/configures to serve as an indicator that a substantial and preferably sufficient amount of saliva has been captured by swabs 12A and 12B so that upon insertion of the swab assemblies (1) strips 7 are activated to provide a quick screening for target substances/analytes, etc., and saliva is captured in vial 15 for subsequent laboratory/confirmation testing if needed or desired. Preferably, indicator strip 27 is visible to an observer and/or subject and provides a confidence indicator that sufficient saliva has been captured prior to insertion of swab assemblies 5A and 5B into housing 2.

Figure 8:
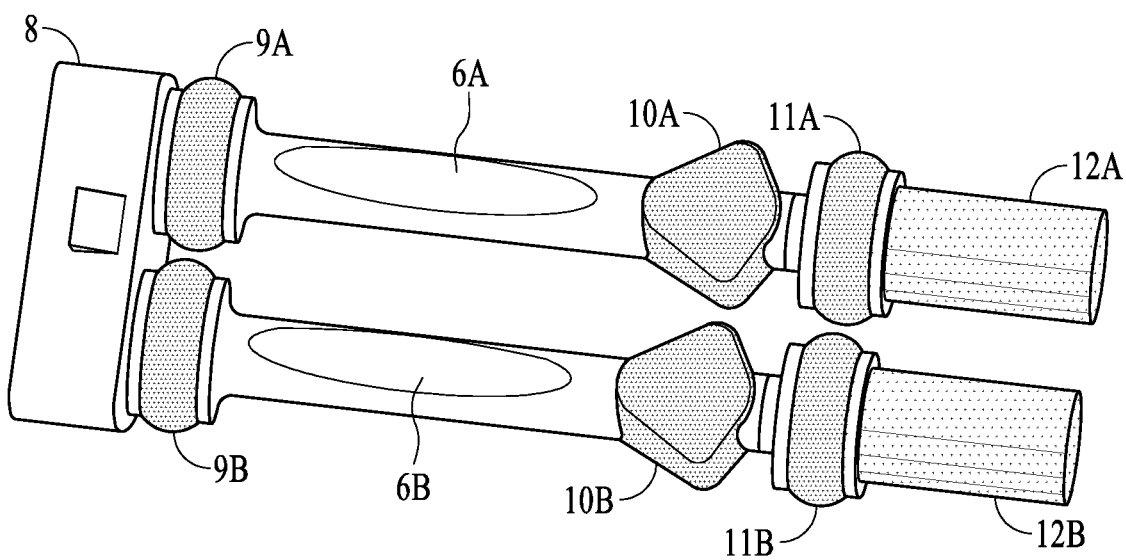
FIG. 8 illustrates a dual swab assembly in accordance with certain preferred embodiments of the present invention.

As will be understood, the present invention encompasses both Single and Dual Swab Devices. In a Single Swab Device, swab tube 2A, swab assembly 5A, vial 15, etc. are not included, and thus housing 2 may be smaller (and not, for example, include the lower skirt portion that surround and protects vial 15. In preferred embodiments, however, both Single and Dual Swab Devices are provided with a common swab assembly (such that robotic equipment may be commonly used for production of both Single and Dual Swab Devices), and a dual swab assembly is produced by securing two single swab assemblies 5A and 5 with dual stem handle 8 (see, e.g., FIG. 7). Having a single swab assembly commonly used for Single and Dual Swab Devices with a locking swab step handle (such as with locking tab 8B, which locks into a corresponding feature of swab stems 6A and 6B, such as illustrated and/or described elsewhere herein) provides significant advantages in assembly cost and time. FIG. 8 is a view of a dual swab assembly using dual stem handle, shown an exemplary locking tab for securing permanently (absent breakage) two single swab assemblies into a dual swab assembly. As will be understood, stem handle 8 is adapted to having an opening and locking mechanism to secure only one swab assembly in Single Swab Device embodiments, as will be understood by one of skill in the art.

The present invention may utilize a wide variety of strips as desired for the particular application. In one additional attribute, a strip testing for THC (parent or metabolite) is positioned in proximity to the opening to swab tube 2B so that saliva may be initially forced onto the THC sensing strip. Increased efficiency of THC testing is an important attribute of the present invention. See other description elsewhere for additional exemplary strips and analytes, etc.

Figure 9:
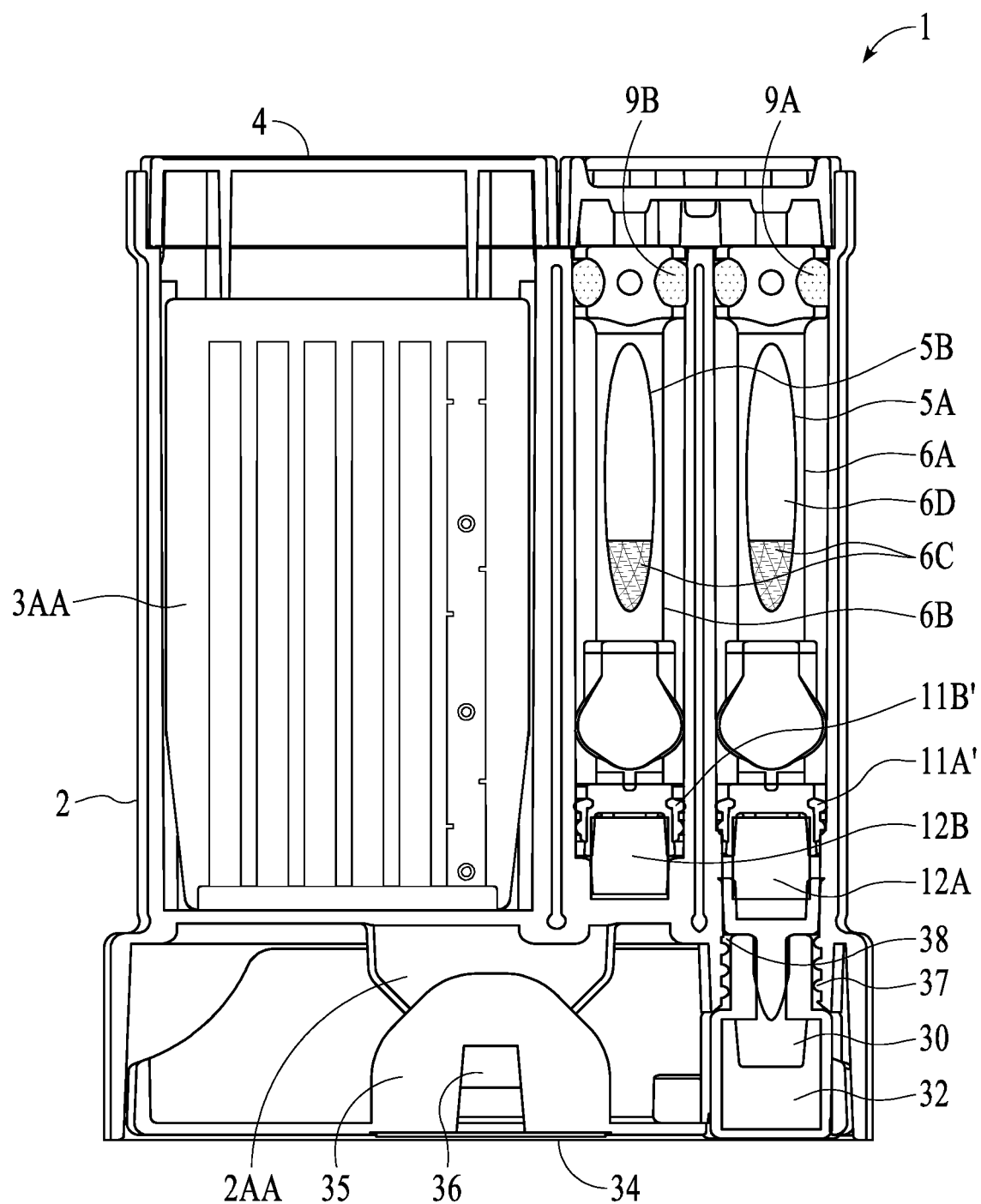
FIGS. 9-10 illustrate overall device views of a fluid sample collection and testing device in accordance with additional certain preferred embodiments of the present invention.
Figure 10:
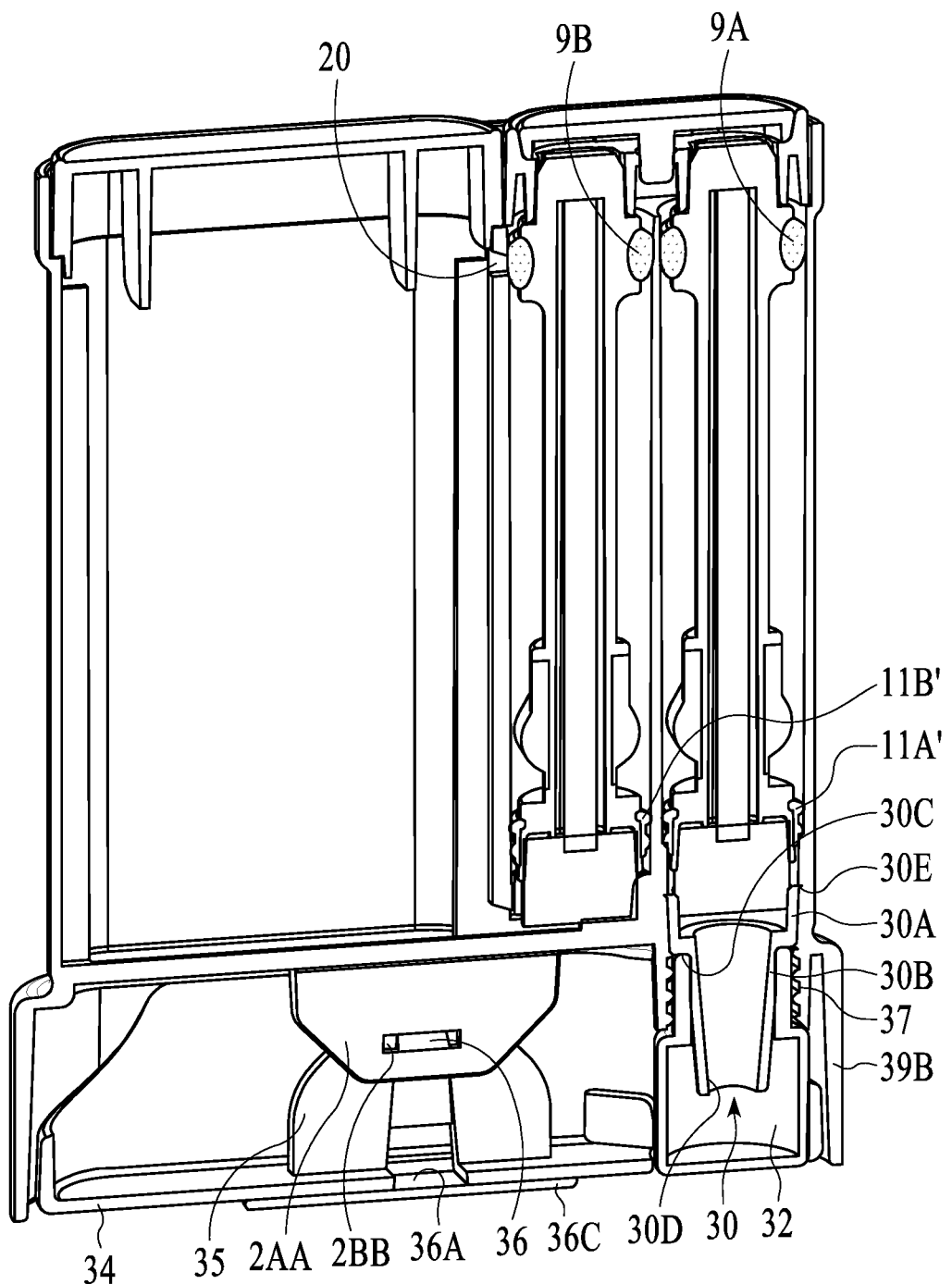

Referring now to FIGS. 9-19, additional exemplary preferred embodiments will be described. As illustrated in FIG. 9, housing 2 in alternative preferred embodiments include interior tabs 2AA near the bottom of housing 2. Tabs 2AA extends downward in a bottom cavity portion of housing 2 as also illustrated in FIG. 10, and includes openings 2BB. Such preferred embodiments preferably include bottom cap 34, which includes tabs 35 with projections 36 (in certain preferred embodiments two of such projections 36 are provided), and projections 36 engage with openings 2BB such that bottom cap 34 preferably is locked onto housing 2. In such preferred embodiments, bottom cap 34 includes key opening 36A, into which a key or tool (illustrated by dotted lines 36B in FIG. 13) may be inserted to cause projections 36 to disengage from openings 2BB such that bottom cap 34 may be removed from housing 2. In certain preferred embodiments, tape 36C (which may be an adhesive or other blocking material that is puncturable) covers opening 36A, thereby providing evidence of tampering or lack thereof. In operation, tool 36B (or other protrusion) punctures tape 36C in order to engage projections 36 (in order to remove bottom cap 34). In this manner, vial 32 (similar to vial 15, described elsewhere herein) may be accessed for removal, such as for having a laboratory confirmation of the preferably oral fluid sample there preferably using an LC MS machine, by puncture of tape 36C and removal of bottom cap 34. Intact tape 36C is evidence that the unit has not been opened or tampered with.

Figure 13:
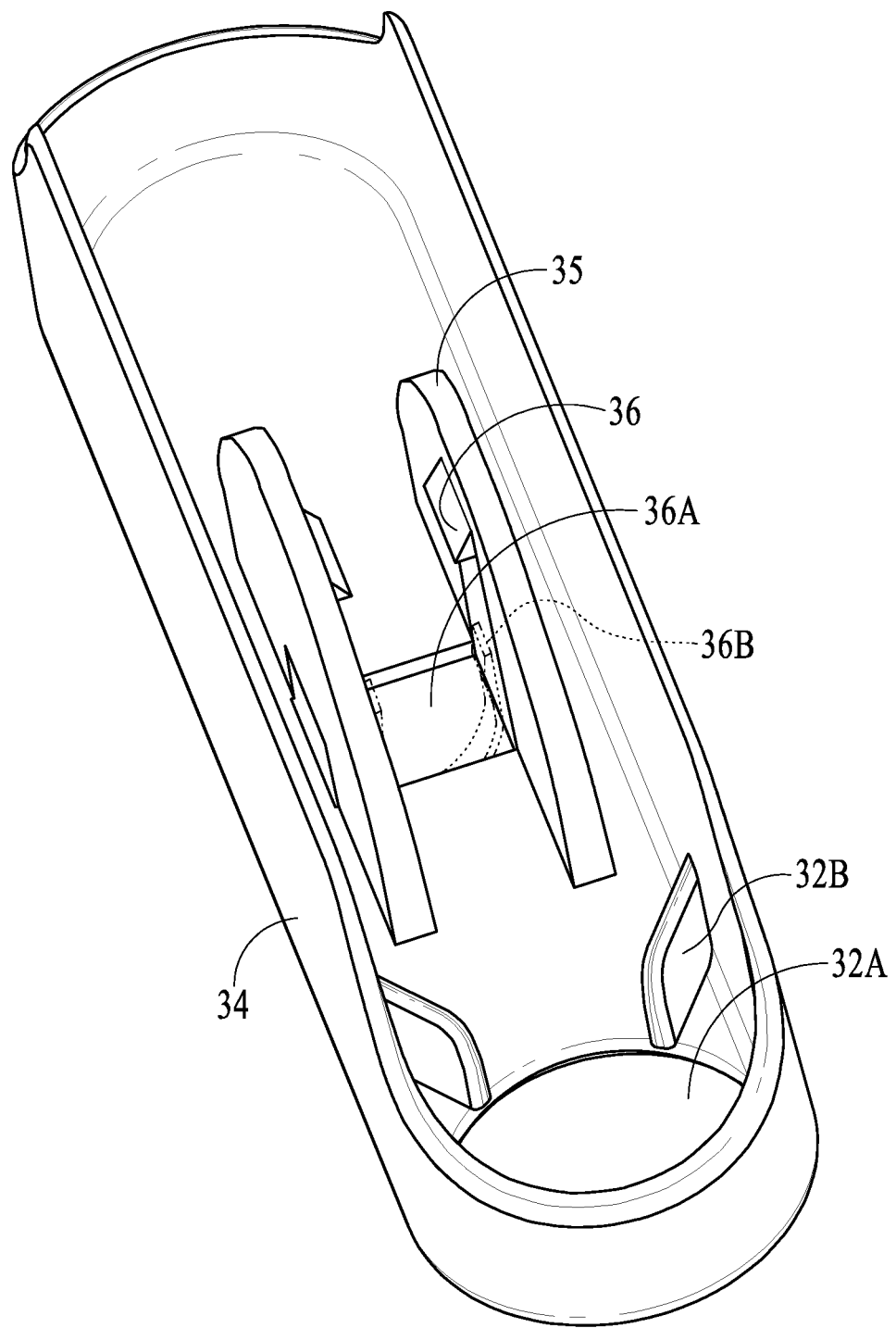
FIG. 13 illustrates a lockable bottom cap for a fluid sample collection and testing device in accordance with additional certain preferred embodiments of the present invention.

Additional details of bottom cap 34 are shown for illustrative purposes in FIG. 13, which illustrates tool 36B (shown as dotted lines in FIG. 13 to illustrate a member that is inserted into opening 36A to spread projections 36 to facilitate removal of bottom cap 34) engaging tabs 35 to cause movement of projections 36 (so as to disengage from openings 2BB). Tool 36B is illustrated to have two parallel or substantially parallel projecting members (shaped much like a flat head screwdriver tip) that engage with tabs 35. The precise shape may vary; what is important is that tool 36B be projectable through hole 36A and cause movement of projections 36 to enough bottom cap 34 to be removed via the tool. Bottom cap 34 preferably (but optionally) includes opening 32A into which the bottom end of vial 32 extends, facilitating viewing of vial 32 from the bottom, etc. Ribs or members 32B are provided to engage vial 32 and help ensure that vial stays securely in housing 2 (and is not, for example, loosened such as by vibration during transport of the device). Contact between ribs/members 32B put pressure on vial 32, causing vial 32 to resist rotational unthreading from housing 2. Vial 32 is secured to housing 2 via threads 37 (similar to threads described elsewhere herein).

Figure 11A:
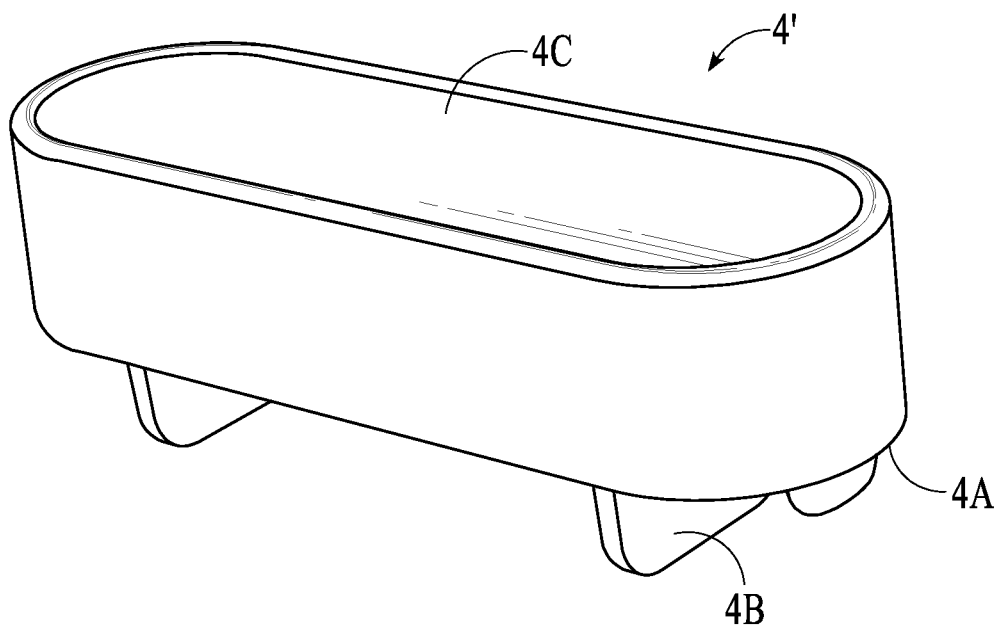
FIGS. 11A and 11B illustrate a top cap preferably sonic weldable in accordance with additional certain preferred embodiments of the present invention.
Figure 11B:
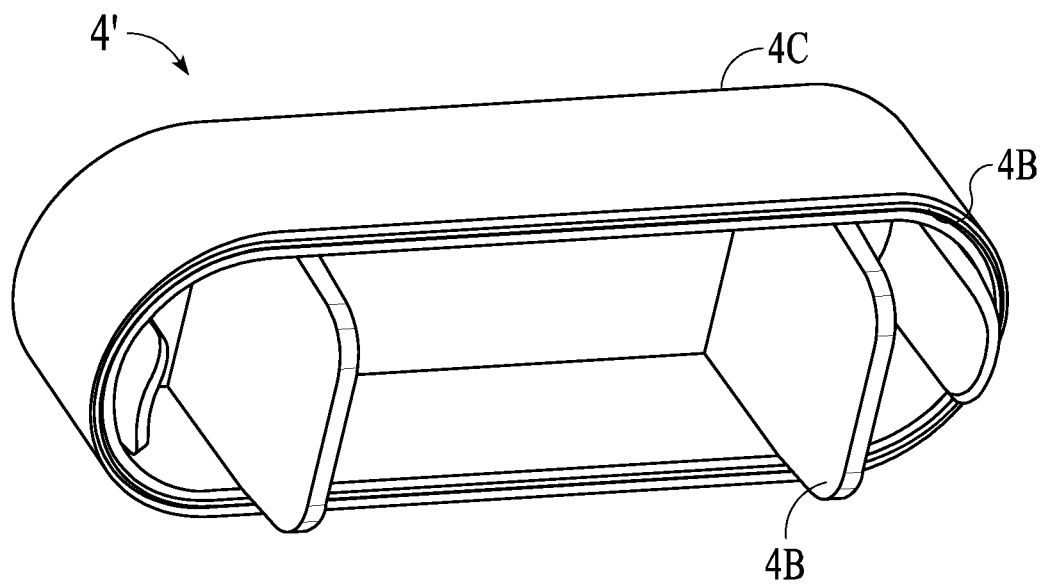

Referring again to FIG. 9 and also FIGS. 11A and 11B, alternative upper body top cap 4' is illustrated. Top cap 4' preferably has a flat top 4C as illustrated and preferably includes tabs 4B extends downward to engage strip card/carrier (or cassette) 3, helping to hold cassette 3 in place so that the bottom tips of the strips carried by cassette 3 are positioned in proximity to the bottom of test chamber 2C of housing 2 so as to contact oral fluid when the device is in operation. Top cap 4' preferably includes sonic welding energy director surface 4A, which engages housing 2 so that it may be adhered to housing 2 preferably by sonic welding. While adhesives or other securing elements may be used to secure top cap 4' to housing 2, it has been determined that sonic welding preferably provides a low cost and air and water tight secure securing mechanism, also providing tamper resistance to the strips within test chamber 2C (venting is provided by opening 20, sealed by seal 11B, such as described elsewhere herein).

Referring again to FIG. 9, swab assemblies 5A and 5B are illustrated in a downward and locked position. Also as illustrated, each of swab stems 6A and 6B include saliva indicator strips 6D (similar to indicator strip 27 described elsewhere herein), each of which includes a color changing region 6C, which preferably changes (for example) from a first color (e.g., white) to a second color (e.g., red) when oral fluid wicks up from the swab absorbent tip (swabs 12A and 12B) onto strips 6D in swab stems 6A and 6B. In preferred embodiments, indicator strips 6D enable an indication of adequate oral fluid being absorbed in swabs or sponges 12A and 12B (see also FIGS. 1-6C) such that oral fluid will contact test strips in cassette 3 and occupy a substantial volume of vial 32 when swab assemblies 5A and 5B are inserted and locked into housing 2. As illustrated, indicator strips 6D (or 27) may have color changing region 6C on one of the indicator strip, and in preferred embodiments color changing regions 6C on both swabs of a Dual Swab Device face commonly in an up or down direction as illustrated.

Referring again to FIGS. 9 and 10, further sealing attributes of the additional exemplary preferred embodiments will be described. As described previously, seals 9A, 9B, were provided at the upper portion of swab stems 6A and 6B, which will be understood to provide a seal to the outside from the interior of both swab tubes 2A and 2B by pressure contact with the walls of swab tubes 2A and 2B by seals 9A and 9B. Seal 9B serves the additional purpose of sealing opening/vent 20 when swab assemblies 5A and 5B are in a fully inserted and preferably locked position in housing 2. As will be appreciated from the drawings and the description herein, Seals 9A and 9B are adapted to form a type of stopper seal, or a rounded contour seal, for opening/vent 20 and the tops of swab tubes 2A and 2B. In the previously described exemplary preferred embodiments, lower seals 11A and 11B are formed similarly to seals 9A and 9B. In alternate exemplary preferred embodiments, sealed 11A and 11B are formed in a different manner.

FIGS. 9 and 10 illustrate lower seals 11A' and 11B' (shown in cross section) having a shape adapted to form a sliding seal (rather than a stopper seal). Applicants have determined that in certain embodiments having a sliding type or syringe type lower seal enables swab assembly insertion into the swab tubes with reduced friction or resistance. As illustrated in such embodiments, seals 11A' and 11B' preferably are formed to have a contoured or textured profile, as compared to the rounded contour of seals 9A and 9B. In one illustrative example, seals 11A' and 11B' have an or more preferably a plurality (two being shown as an example) fins or o-rings (projecting sealing members, etc.), preferably spaced apart as illustrated but formed in a unitary manner, such as by a second shot or overmold injection molding process. Such fins or o-rings provided a sliding seal or a syringe seal to prevent or inhibit fluid travel up as the swab assemblies 5A and 5B are inserted and moved downwardly in swab tubes 2A and 2B. As swabs 12A and 12B are compressed by downward movement of swab assemblies 5A and 5B into swab tubes 2A and 2B and fluid is released from swabs 12A and 12B, pressure builds, and sealing is provided by seals 11A' and 11B' to inhibit upward flow of the fluid towards the top of the housing, thereby facilitating fluid flow into vial 32 and test chamber 2C. At the same time, user experience degrades if the force required to fully insert swab assemblies 5A and 5B is too great, and thus, swab seals 11A' and 11B' are provided in a form that provides an adequate seal with improved slide resistance by having a contoured or finned structure or textured shape. In yet further alternative embodiments, seals 11A' and 11B' are textured in a manner to reduce sliding resistance rather than with projection-style fins or o-rings in a manner to provide a sliding/syringe type seal, again as compared to the stopper type seal of seals 9A and 9B. What is important is that each of seals 9A/9B and 11A'/11B' are adapted and formed optimally for their particular functions, which is understood from the description and drawings provided herein, and preferably formed from the same manufacturing steps, such as a second shot or overmold injection molding process that form both types of seals on swab stems 6A and 6B.

The additional exemplary preferred embodiments illustrated in FIGS. 9-19 also include a vented thread/gasket sealing mechanism, which is further illustrated and described herein. FIGS. 9, 10, 16A-16D, 18A and 18B illustrate gasket 30, preferably shaped much like a funnel, and preferably having extending portion 30D that extends into vial 32 and channels a flow of fluid (which may be oral fluid) into vial 32 as swab 12A is compressed upon insertion into housing 2. Gasket 30 has opening 30F through which fluid passes into vial 32. In a first position illustrated at the height shown by gasket 30 in FIG. 16B, upper portion 30A of gasket is above the top of vial 32 resting on ledge 2G of housing 2, with ledge 2G being a slightly reduced diameter portion of the vial-side housing tube (2H in FIG. 16B, similar to swab tube 2A described elsewhere herein). Lip 30E of gasket 30 rests on ledge 2G, and friction interference between upper portion 30A and the wall of vial side housing tube 2H create a seal inhibiting passage of oral fluid. In this first position, as swabs/sponges 12A and 12B are compressed as swab assembly 5A is inserted and lowered into housing 2, oral fluid is released from swab/sponges 12A and 12B and flows into vial 32 via opening 32F (and test chamber 2C as previously described via a flow communication channel as previously described). Swabs/sponges 12A and 12B are further compressed into the downward pressure position, as illustrated in FIGS. 9 and 10. In the second position, as illustrated in FIG. 16C, gasket 30 preferably has upper portion 30A contacting the side circumferential wall at the lower end of vial tube 2H, under surface 30C downwardly contacting the top circumferential surface of vial 32, and neck surface 30B contacting the inner circumferential wall of the neck portion of vial 32 (on the outside of which via 32 has threads 37 engaging corresponding threads of housing 2 to secure vial 32 to housing 2).

In accordance with preferred embodiments, gasket 30 is formed of a flexible, but relatively rigid, preferably elastomeric material such as TPE (thermoplastic elastomer) or other polymeric or rubber like material. In accordance with preferred embodiments, gasket 30 has a durometer of greater than 50, and more preferably a durometer rating in the range of 70 to 90. In accordance with certain preferred embodiments, gasket 30 is a flexible material having a durometer of 80+/−5-10%. Applicant has discovered that such a composition of gasket 30 desirably allows gasket 30 to hold in the first position while having enough compression to inhibit oral fluid from flowing around gasket 30 while in the first position, but yet release, as pressure increases during downward movement of the swab assemblies 5A and 5B, at a reasonable pressure to move and traverse down swab tube 2H to the second position, thereby bringing surfaces 30B and 30C into contact with the corresponding surfaces of vial 32, and bringing surface 30A into contact with the circumferential wall of vial tube 2H of housing 2 so as to inhibit oral fluid from flowing around gasket 30 while in the second position.

Figure 14:
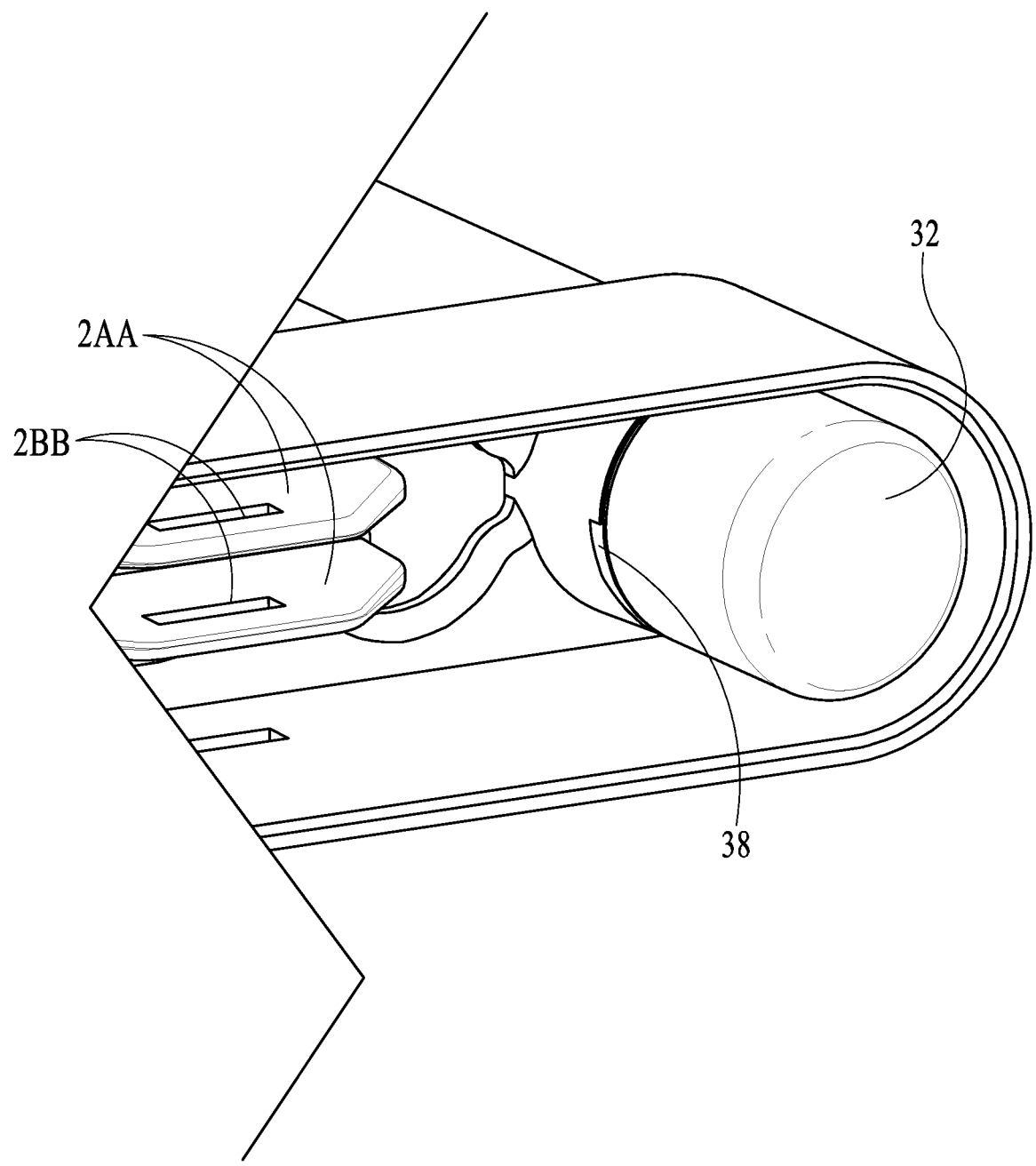
FIGS. 14 and 15 illustrate a vial confirmation stem tube venting implement for a fluid sample collection and testing device in accordance with certain preferred embodiments of the present invention.
Figure 15:
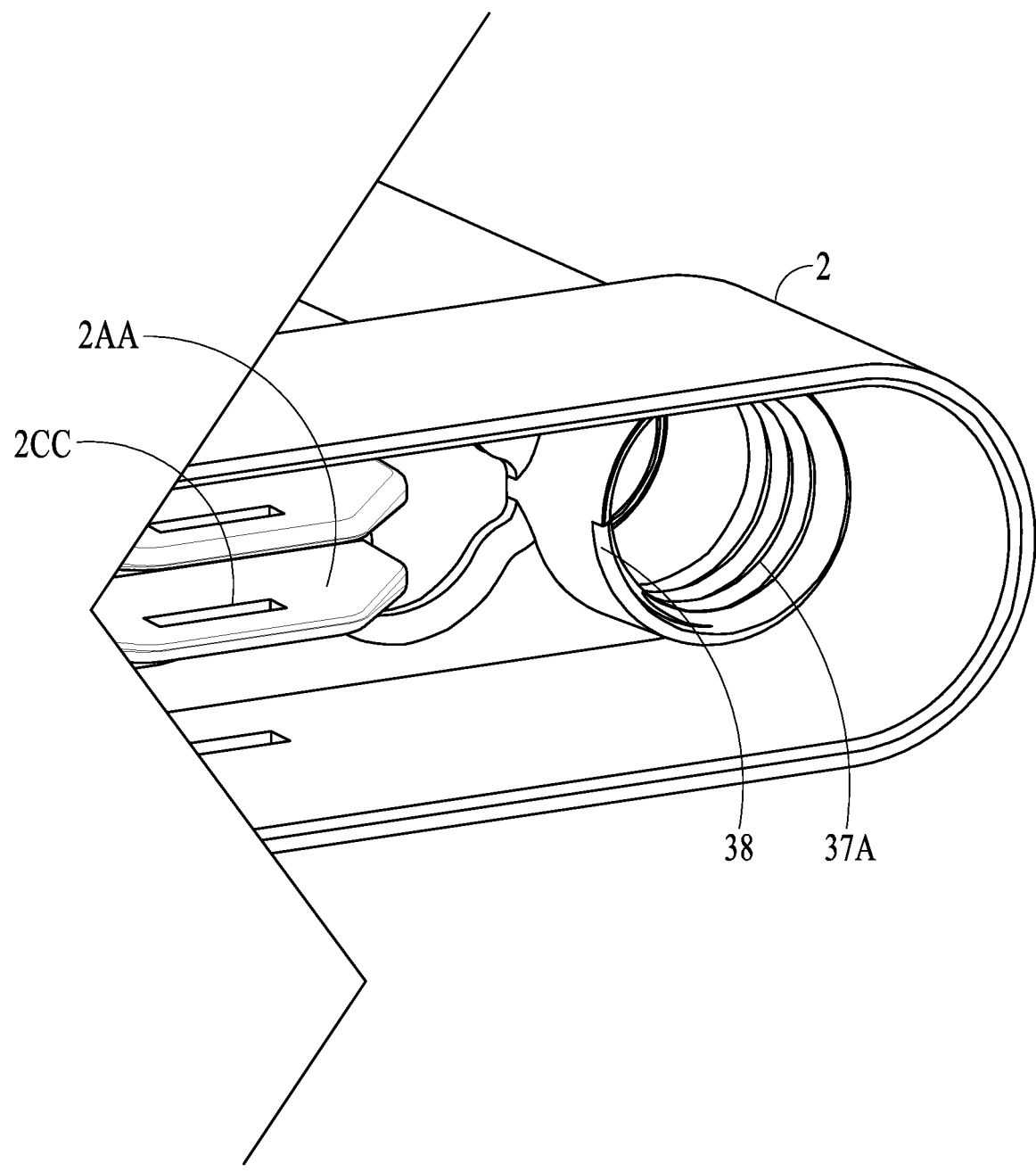

Having gasket 30, housing 2 and vial 32 configured and arranged as illustrated and described herein, certain preferred embodiments utilize improved air venting so as to provide reduced back pressure to a user attempting to push swab assemblies 5A and 5B into locked position in housing 2, and improved fluid extraction efficiency. As illustrated in FIGS. 14 and 15, notch 38 is formed in the lower end portion of threaded wall 37A of housing 2. Notch 38, which may be tapered or contoured, ensures a gap between at least part of the lower end portion of threaded wall 37A of housing 2 (an arrow indicating air flow may be drawn from inside the vial around lower tip 30D and up the neck of vial 32 and around the threads and out notch 38). As vial 32 is secured onto housing 2 using threads 37 of vial 32 and threaded wall 37A of housing 2, the upper lip of vial 32 may contact housing 2 and snug-up to be secure, while notch 38 ensures that there is not an air-tight seal created at this contact point. Notch 38 thus enables air venting via threads 37/threading wall 37A. In accordance with such embodiments, sealing to prevent leaking of oral fluid is achieved via gasket 30 as previously described. Thus, as swabs/sponges 12A and 12B compress, air is vented via notch 38 and threads 37/threaded wall 37A, while fluid flow into vial 32 is facilitated, and an operator experiences less back pressure while pushing the overall swab assembly into its final locked position in housing 2. As will be appreciated, gasket 30 facilitates a linearly movable, two position valve/sealing implement or member, wherein in a first (unsealed, venting) position in swab tube 2A, air vents to the outside of the device, and under pressure of swab compression the gasket linearly moves/traverses down swab tube 2H to a second (sealed/non-venting) position in swab tube 2B, where air does not vent to the outside of the device, and fluid likewise does not escape to the outside of the device.

Figure 12:
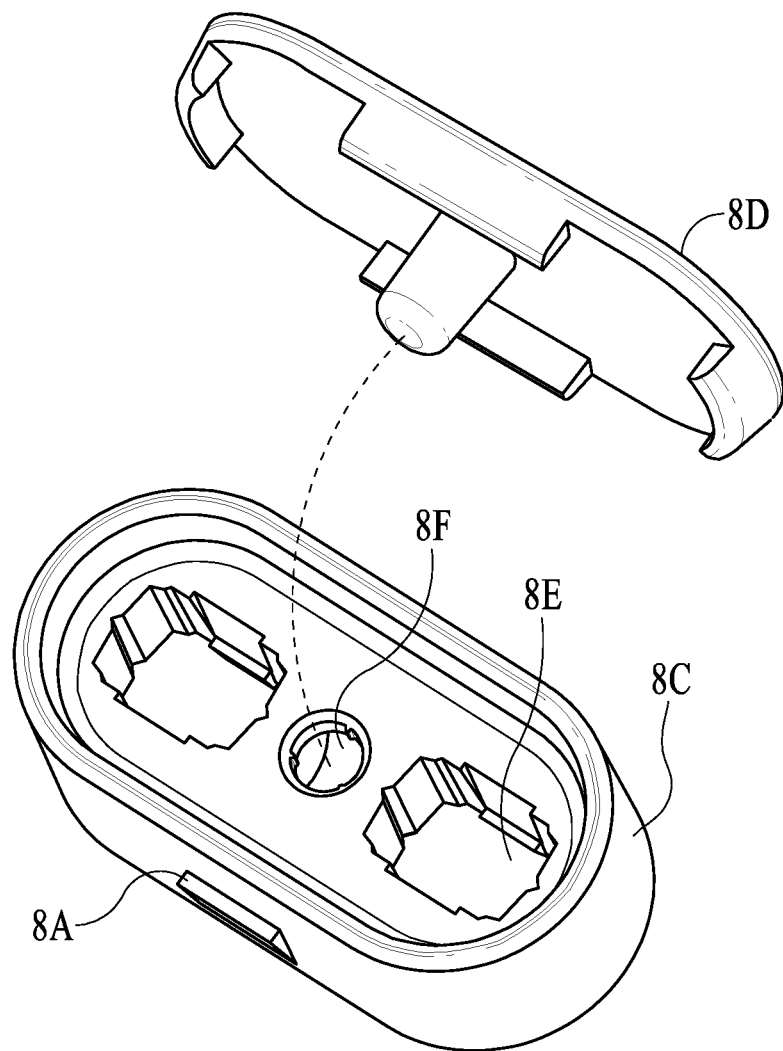
FIG. 12 illustrates a dual swab stem handle for connecting two swab assemblies to make a dual swab assembly and a top cap therefor in accordance with additional certain preferred embodiments of the present invention.
Figure 16A:
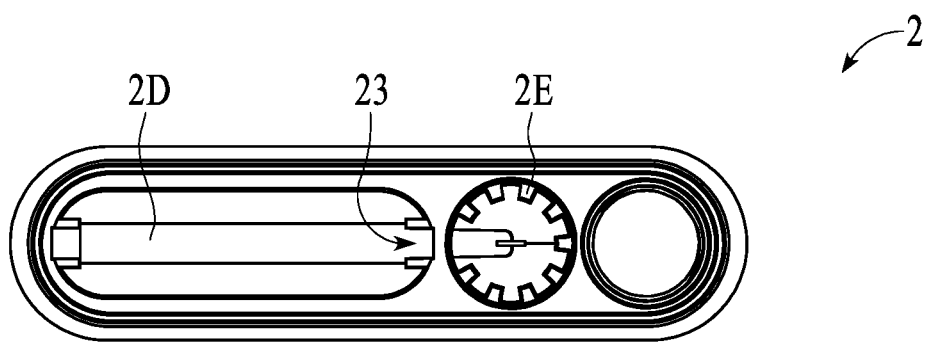
FIGS. 16A-16D illustrate certain floor properties and other attributes of a test chamber and a ventable/sealable gasket for a fluid sample collection and testing device in accordance with certain preferred embodiments of the present invention.
Figure 16B:
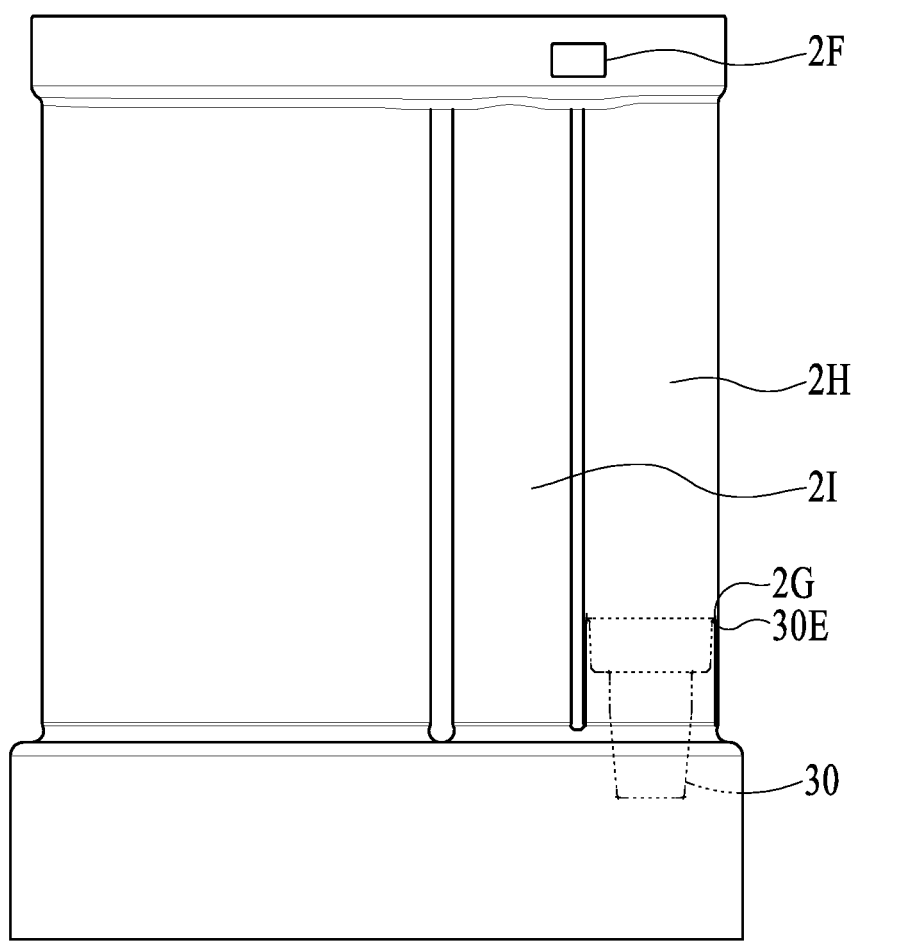
Figure 16C:
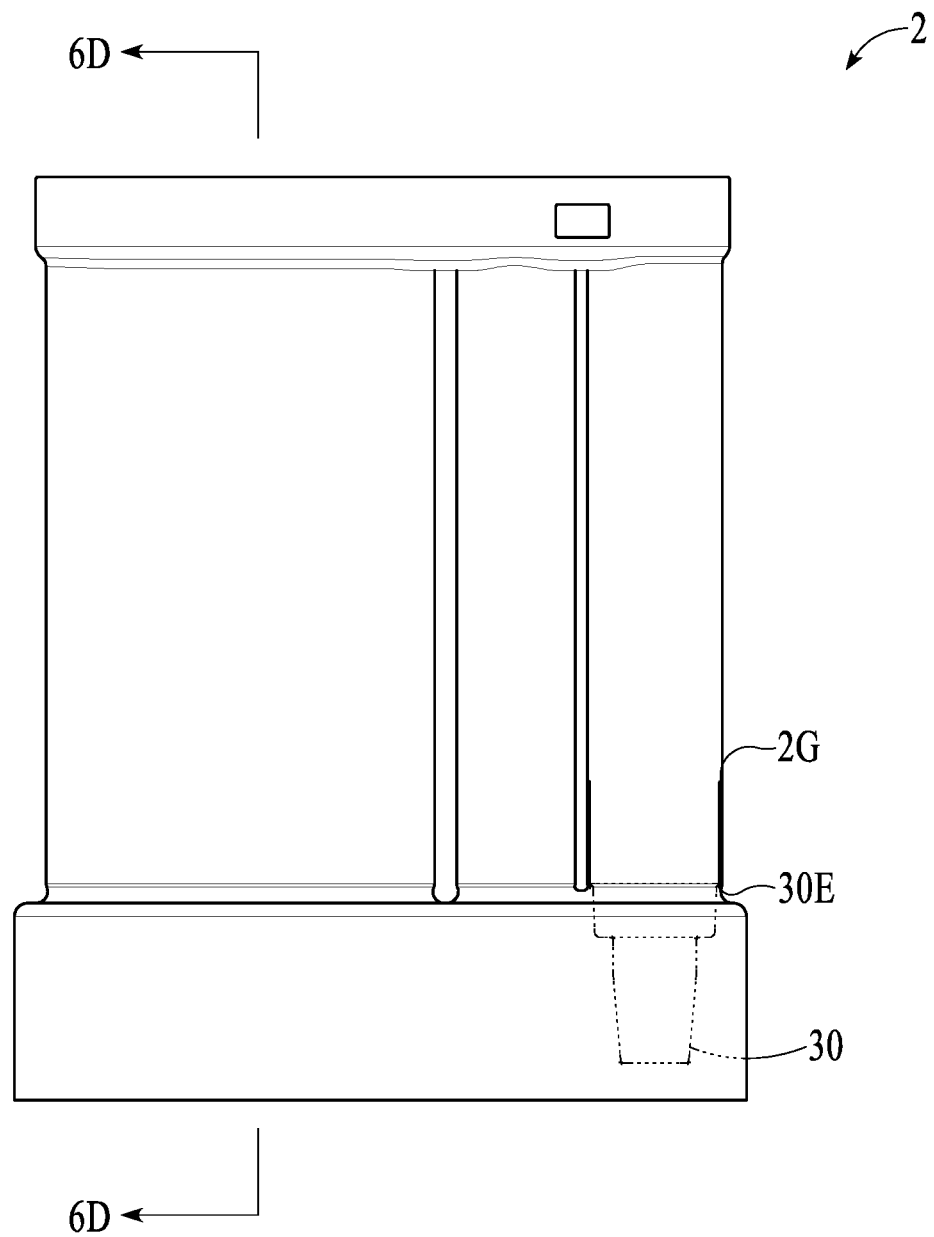

As illustrated in FIGS. 12 and 16B and 16C, housing 2 preferably includes openings 2F into which protrusions 8A on both sides of swab top collar 8C engage to lock the overall swab assemblies into housing 2. As illustrated, protrusions 8A preferably are tapered with an upper ledge to lock into openings 2F of housing 2, while in other embodiments other shapes of protrusions may be utilized. What is important is that the overall swab assembly lock into housing 2 so as to dissuade or prevent swab assembly removal and prevent/inhibit tampering. Also as illustrated, openings 8E are provided to engage with swab stems preferably having a similar protrusion to lock swab stems into place and an opening 8F to ensure a corresponding feature of swab assemble top cap 8D, such as is illustrated in FIG. 12.

Figure 16D:
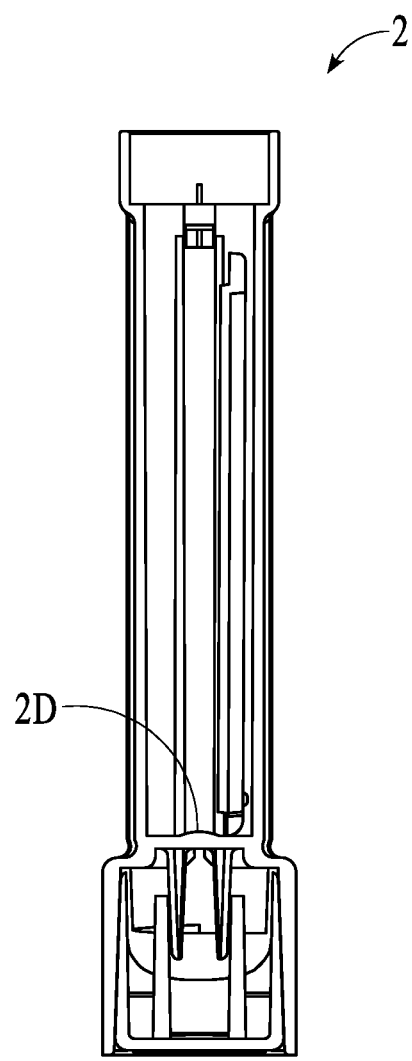

Also as illustrated in FIGS. 16A and 16D, housing 2 preferably has a raised (preferably tapered or contoured) center portion 2D on the floor of housing 2 where the lower end of cassette(s) 3AA (FIG. 9) rest(s). Such a raised center portion floor helps channel fluid from cassette tube 2I of housing 2 to the lower ends of the strips inserted in cassette(s) 3AA by using gravity to flow oral fluid from the center region of test chamber 2C towards its edges where the strip tips preferably are positioned, thereby facilitating testing of the fluid via the strips. Housing 2 of FIGS. 9 and 10 includes passage/channel 23 from tube 2I (similar to swab tube 2B described elsewhere herein) into test chamber 2C of housing 2 containing cassette 3AA and an upper air opening/vent 20 such as previously described in connection with other preferred embodiments. Also, as illustrated in FIG. 16A, the floor of tube 2I preferably includes a plurality of raised bumps 2E to help compress swab/sponge 12B to facilitate release of oral fluid from swab/sponge 12B and movement to passage/channel 23 from tube 2I into the cavity containing cassette 3AA. See FIGS. 3 and 4 and related description regarding passage/channel 23 and opening/vent 20.

Figure 17:
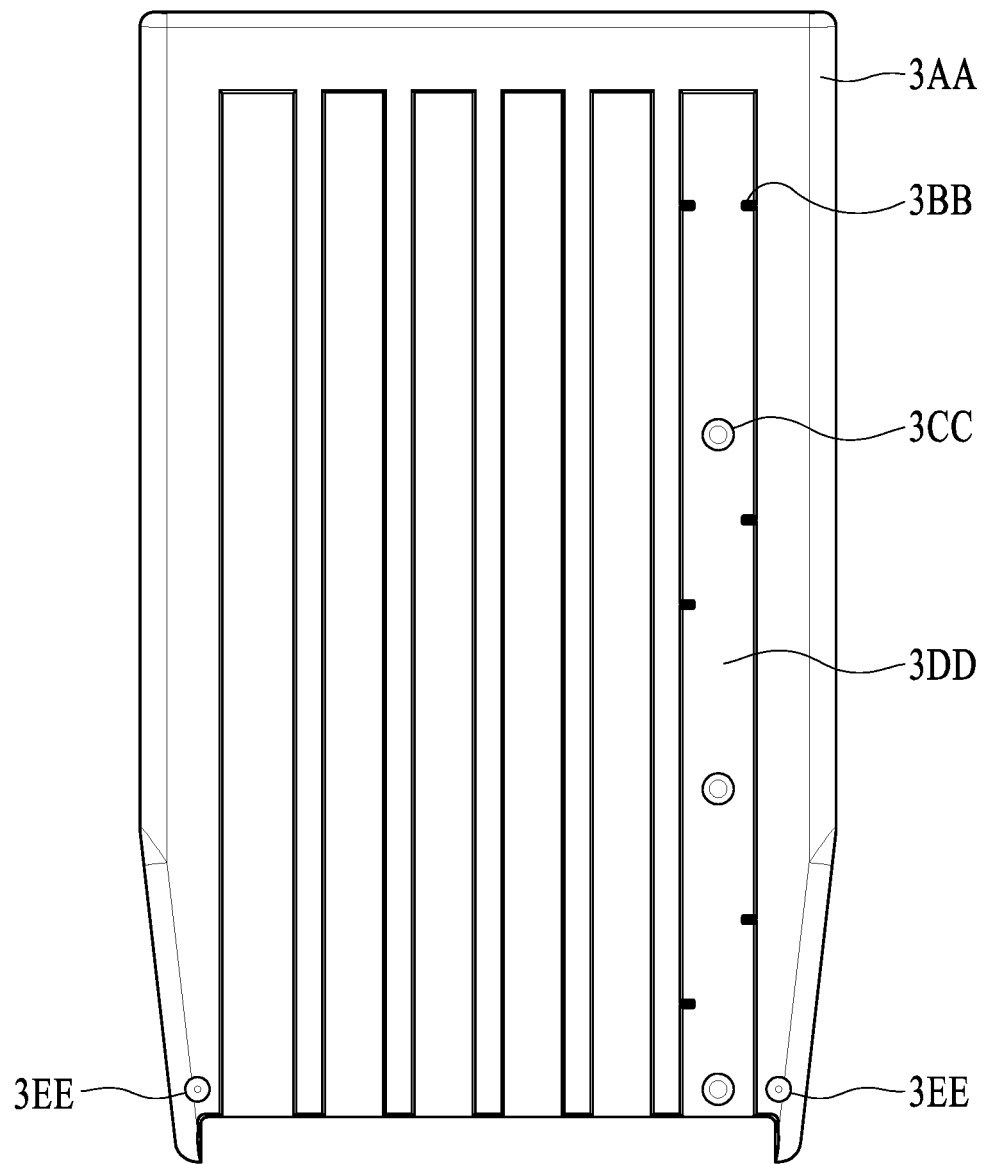
FIG. 17 illustrates an improved cassette for holding test strips for a fluid sample collection and testing device in accordance with certain preferred embodiments of the present invention.
Figure 18A:
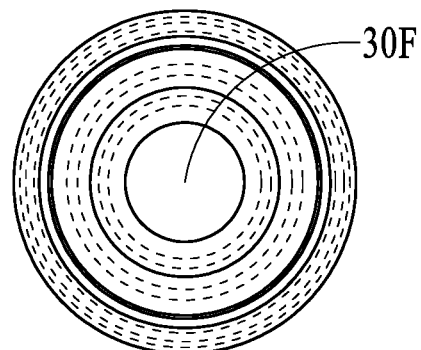
FIGS. 18A-18B illustrate a ventable/sealable gasket for a fluid sample collection and testing device in accordance with certain preferred embodiments of the present invention.
Figure 18B:
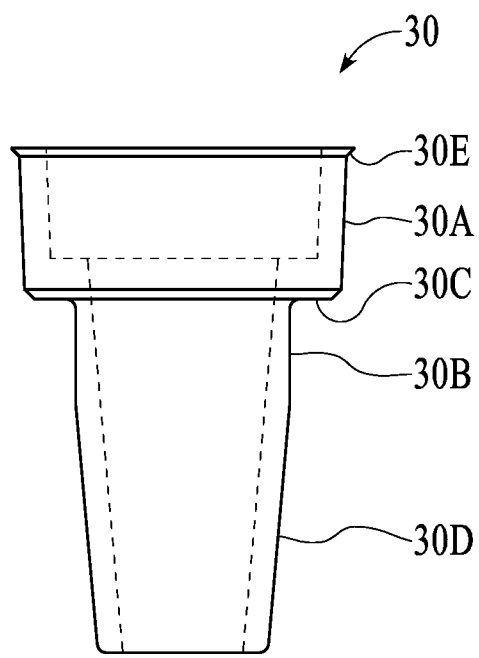

FIG. 17 illustrates an alternative preferred embodiment of a cassette for holding test strips having one or more channels, generally illustrated and described herein as cassette 3AA. It should be understood that the present invention contemplates embodiments including one or two such cassettes 3AA (or similar cassettes) on one or both sides of housing 2 as will be understood by those of skill in the art. As illustrated in FIG. 17, rightmost channel 3DD (a channel being a receptacle or holding area for a test strip) includes bumps or islands 3CC (three such bumps or islands 3CC shown in this exemplary embodiment) that causes the strip to be raised from the bottom floor of channel 3DD. In this manner, the backside of the strip has a spacing from (and thus reduced contact with) the material (preferably plastic) comprising cassette 3AA. In addition, channel 3DD includes side protrusions 3BB to position the strip so that the sides of the strip do not contact side walls of channel 3DD. Side protrusions 3BB preferably are on opposite sides of channel 3DD but preferably not directly across from each other as illustrated (in other embodiments, side protrusions 3BB are directly opposite each other). In this manner, the side edges of the strip have a spacing from and do not contact the side walls of the material comprising cassette 3AA. With the combination of bumps/islands 3CC and side protrusions 3BB, the strip more nearly floats in channel 3DD with reduced contact with the material comprising cassette 3AA. As will be understood by those of skill in the art, a label generally is provided to cover the strips as positioned in cassette 3AA. Applicants have determined that cassette 3AA having one or more (including up to all) channels of cassette 3AA constructed as shown provide improved detection of substances such as THC. In accordance with certain preferred embodiments, the strip for detecting the presence or absence of THC is positioned in a channel such as channel 3DD positioned on a rightmost or leftmost channel of cassette 3AA (having a plurality of channels, such as the 6 channels shown in FIG. 17 or the 7 channels illustrated in FIGS. 1 and 2) so as to more optimally contact oral fluid. In alternative preferred embodiments, all such channels of cassette 3AA have bumps/islands 3CC and side protrusions 3BB as is shown for channel 3DD of FIG. 17.

In preferred embodiments, cassette 3AA also includes bumps 3EE, which serve to position cassette 3AA away from front face of housing 2, which has been determined to reduce capillary rise of fluid upwards between cassette 3AA and housing 2. In this embodiment, bumps 3EE may contact the front face of housing 2, while the main face of cassette 3AA is spaced apart from, and does not contact, the front face of housing 2. Additionally, as illustrated cassette 3AA may optionally have side legs having a tapered or beveled shape, so as to have a smaller dimension at the bottom of the legs and a larger dimension at an upward portion of the legs. In this manner, the smaller dimension is presented to fluid at the bottom of test chamber 2C, further reducing the incidence of capillary rise or fluid contact with the material of cassette 3AA.

Figure 19:
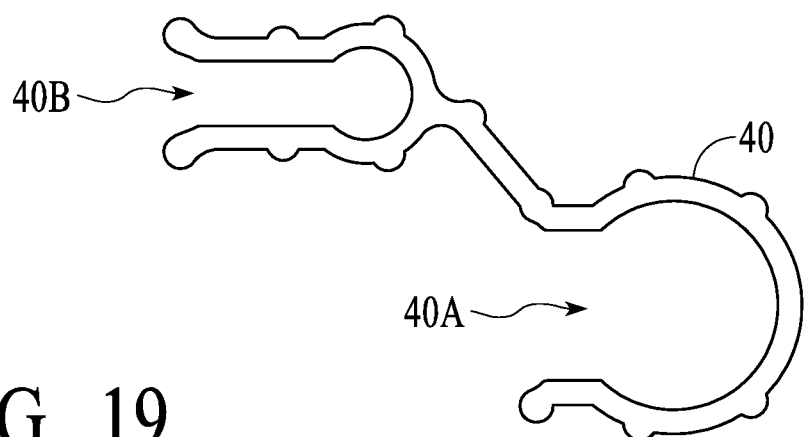
FIG. 19 illustrate a swab assembly-housing holding clip for a fluid sample collection and testing device in accordance with certain preferred embodiments of the present invention.

As illustrated in FIG. 19, holding clip 40 is provided so that a complete swab assembly such as shown in FIG. 8 may be secured by clamp 40B, while clamp 40A clamps to vial tube 2H. In this manner, the complete swab assembly is secured to the outside of housing 2 so that the swab assembly/housing combination may be run through an automated pouching machine. In accordance with such alternative preferred embodiments, the swab assembly may be packaged in a plastic bag for hygienic considerations, and yet secured to housing 2 in a manner suitable for automatic pouching.

Applicants' exemplary embodiments expressly include the Single Swab Device, adapted to leave off the confirmation vial side of the device, including the swab tube and swab assembly in fluid communication with the confirmation vial. Thus, attributes of housing 2, test chamber 2C, opening/vent 20, channel 23, seals 9B, 11B, 11B', etc., are desirably utilized with the Single Swab Device, as well as cassette 3AA and its variations as described and shown herein.

In accordance with yet other embodiments of the present invention, a Vial-Side Only Device is contemplated, which in essence may incorporate only the vial side of the device, including the swab tube and swab assembly in fluid communication with the confirmation vial. Thus, the description related to the vial side of the device is applicable to such Vial-Side Only embodiments and is hereby incorporated by reference. As will be understood by those of skill in the art, the plastic molding and component fabrication would be adapted to produce only the vial side of the device, with, for example, a top and bottom cap each adapted for just the vial side, using only a single swab (which preferably may be implemented in a manner consistent with the disclosed embodiments of the swab assemblies for the Dual Swab Device).

Figure 20:
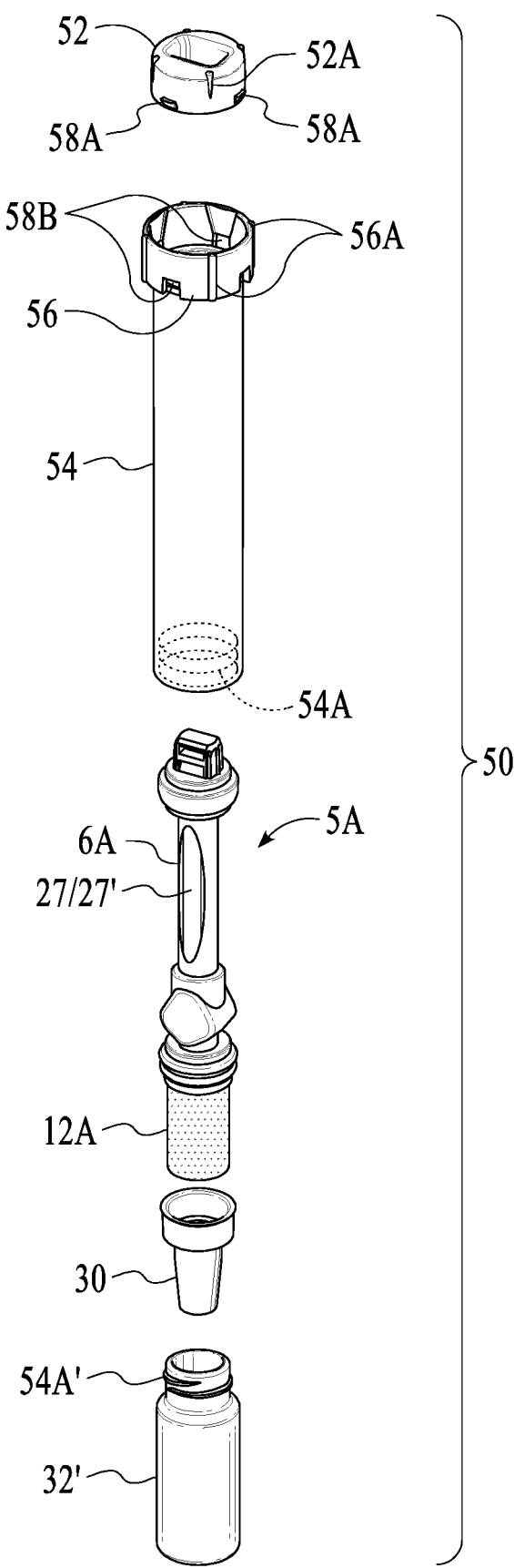

Refinements for such a Vial-Side Only Device are used in accordance with other exemplary preferred embodiments, one such embodiment being illustrated in FIG. 20, which is an exploded view of such embodiment. As illustrated, top cap 52 snaps onto the top of swab assembly 5A, which will thereafter be pushed into tube 54 when the device is run by a user (see explanation elsewhere herein). Top cap 52 includes tabs 58A having an upper ledge and tapered bottom to engage openings 58B of collar 56 of tube 54 when swab assembly 5A is "snapped" into final position. Preferably, the engagement of tabs 58A and openings 58B produces an audible snap sound, which (1) ensures that swab assembly 5A is fully inserted into tube 54, and (2) locks swab assembly 5A in position so that back pressure or inadvertent user operation does not cause swab assembly 5A to undesirably back out of tube 54. Collar 56 has slanted portions 56A of a larger dimension at the top to guide tabs 58A to engage with openings 58B. To aid in alignment of top cap 52 and tube 54 when a test is run, alignment marks 52A and 56A are provided on top cap 52 and collar 56 of tube 54 as illustrated. Four pairs of tabs 58A and openings 58B are in the illustrated embodiment, but other sizes, shapes, numbers and configurations of locking mechanisms are used in alternative embodiments. What is important is that a first feature(s) on top cap 52 engage with a corresponding second feature(s) on some portion of tube 54 so that swab assembly 5A may be desirably locked in place such as described herein.

Also as illustrated in FIG. 20, tube 54 secures vial 32' via threads 54A inside of tube 54 and threads 54A' on the top of vial 32', which rotationally engage as will be understood to those of skill in the art. Preferably, vial 32' (and threads 54A'), tube 54 (and threads 54A) have a notched feature as described in connection with the embodiments illustrated in FIGS. 9, 10, 14, 15, 16B, 16C, etc., such disclosure being directly applicable to the embodiment illustrated in FIG. 20. What is important is that gasket 30 engage with tube 54 and vial 32' to provide a venting/sealing mechanism as described elsewhere herein.

Also, as illustrated in FIG. 20, indicator strip 27 is provided in the stem of swab assembly 5A, thereby providing an indication of adequate fluid absorption in swab 12A (sponge like material, as described elsewhere herein), or at least a confidence measure that sufficient fluid has been absorbed. Also as illustrated in FIG. 20, an analyte detecting strip 27' (similar to strips 7 and other strips as described elsewhere herein) optionally is included in stem 6A of swab assembly 5A. Thus, two or more strips such as strip 27 and 27' may be provided in stem 6A of swab assembly 5A. In one embodiment, only indicator strip 27 is present in stem 6A; in another embodiment, indicator strip 27 is present and in a back-to-back configuration strip 27' also is present (e.g., a strip for detecting opioids or other drugs of abuse, or viruses or other analytes, antibodies, etc.). In yet another embodiments, two of strips 27' are provided, preferably in a back-to-back configuration. In such embodiments, for example, one or more drugs or diseases may be detected in a rapid scan fashion by strips 27', while vial 32' captures an oral fluid sample for subsequent laboratory, confirmation or other testing. Thus, the embodiment of FIG. 20 encompasses alternatives including a rapid scan with strips, while capturing a sample for subsequent laboratory testing.

Also, the embodiment of FIG. 20 is contemplated for use in capturing a sample that may be used for genetic testing, genetic identification, virus or disease detection, drug or other analyte detection, etc., with or without strips 27/27'. All such disclosures relevant to such applications provided elsewhere herein should be understood to be as applicable to the embodiments described in connection with FIG. 20.

Also, it will be understood that vial 32' may be used a buffer or preservative material, such as preserving genetic material of cells, viruses, other pathogens or the like. In an exemplary workflow relevant to the embodiment of FIG. 20 (and also other embodiments), a user may be provided with tube 54 including gasket 30, an unused swab assembly 5A, and vial 32' separate from tube 54 containing a liquid or solid buffer/preservative (e.g., for deactivating a virus while preserving RNA), preferably secured in vial 32' with a screw cap (not shown, but well understood in the art). The user puts swab assembly 5A in his/her mouth to absorb oral fluid (preferably vigorously rubbing the tongue, back of the tongue, checks, inner lips, under the tongue, etc.) and cellular and other material, or which otherwise attach to swab 12A. Before, during or after the fluid, etc. absorption process, the user unscrews the cap, secures vial 32' (containing the optional buffer/preservative) to tube 54 via threads 54A/54A' in a rotational, know manner). After, for example, confirming adequate oral fluid absorption via indicator strip 27 (and/or via analyte strip 27'—which may include a rapid scan test of one or more target analytes, pathogens, etc.), then the user inserts swab assembly 5A into tube 54 and pushes down to engage tabs 58A and openings 58B (as previously described), with gasket 30 funneling fluid into vial 32' in a first/venting position, which moving under pressure to a second/sealing position (all as described elsewhereherein). The entire device may then be delivered to a laboratory (via hand delivery or a courier/delivery service), where the neat (unbuffered) or buffered/reserved sample in vial 32' may be analyzed with laboratory instrument (e.g., LC MS) for confirmation, viral agent, genetic detection/analysis, etc. As will be appreciated, oral specimens may be readily obtained in a convenient manner in a variety of settings, with a rapid scan optionally provided, and with a sample ready for laboratory analysis such as for detecting viruses (e.g., influenza, COVID-19 or other coronaviruses, cancer, HIV, hepatitis, drugs of abuse, genetic information, or other markers or information obtainable via oral fluids).

Exemplary buffers for such a workflow include, but are not limited to, saline, saliva DNA preservation buffer, sodium citrate, a citrate-containing buffer, sodium azide, virus cell-lyse storage buffer (e.g., a buffer having a lysis effect on, for example, a virus, while preserving RNA information), and the like. Any such buffer/preservative, particularly for use in the workflow described above, are within the scope of embodiments of the present invention.

As will be understood by those of skill in the art, teachings from co-pending U.S. application Ser. No. 15/417,905, which has been incorporated by reference herein, are generally applicable to the exemplary preferred embodiments set forth herein. By way of additional explanation and not by way of limitation, certain of such teachings are set forth below.

Analyte Screening

An embodiment of the present invention provides an analyte screening device which includes a rapid screening, lateral flow chromatographic immunoassay for the simultaneous, qualitative or quantitative detection of analytes in a fluid sample. For example, without limitation, the fluid sample may be saliva, urine, blood, mucus, water, or fluid extract of a solid or a semi-solid, for example stool or mucus or liquid biopsy. The fluid sample may also be an environmental sample, for example, without limitation, soil, dust, water, plant matter, insect, animal matter, or a fluid extract of any of the foregoing. The fluid sample may also be a food or beverage, for example, without limitation, a liquid beverage, a liquid-containing food, or a fluid extract of a solid, semi-solid or powdered food or beverage. The fluid sample may also contain genomic or proteomic material for testing and analysis.

An embodiment of the invention includes at least one membrane test strip, in fluid communication with a sample receiving member, able to indicate the presence or absence of at least one analyte above or below a threshold concentration in the fluid sample using a lateral flow chromatographic assay.

In an embodiment of the invention, the lateral flow chromatographic assay is a competitive assay, in which an analyte in the fluid sample competes with a competitor for binding with an anti-analyte antibody. For example, the anti-analyte antibody may be labeled, and the competitor may be immobilized in the test region of the membrane test strip. After the fluid sample reaches the dye region, it encounters the labeled anti-analyte antibody. If the analyte is present in the fluid sample above a predetermined threshold concentration, the analyte will saturate the binding sites of the labeled anti-analyte antibody; otherwise, some or the entire labeled anti-analyte antibody remains free to bind the competitor. As the fluid sample migrates along the membrane test strip by capillary action, it carries the labeled anti-analyte antibody along until it reaches the test region. The test region contains the immobilized competitor, which may be the analyte, fragments of the analyte, epitopes of the analyte, molecular mimics of the analyte, anti-idiotypic antibodies, or any other molecule able to compete with the analyte for binding to the anti-analyte antibody. If the analyte is present above the predetermined threshold concentration, the labeled anti-analyte antibody is saturated and does not bind the immobilized competitor, resulting in no signal in the test region; otherwise, the anti-analyte antibody is unsaturated and can bind to the competitor, resulting in a signal in the test region.

Thus, according to an embodiment of the invention employing a competitive assay, an analyte-negative fluid sample (containing lower than the predetermined concentration of the analyte) will generate a line in the test region due to capture of the labeled anti-analyte antibody, whereas an analyte-positive fluid specimen will not generate a colored line in the test region because the analyte in the fluid sample will saturate the labeled antibody and thus prevent its capture in the test region.

In an embodiment of the invention, the lateral flow chromatographic assay is a sandwich assay, in which the analyte must be present for the labeled anti-analyte antibodies to be captured in the test region. For example, the analyte antibody may be a labeled antibody, and a second anti-analyte antibody may be immobilized in the test region. For example, after the fluid sample reaches the dye region, it encounters the labeled anti-analyte antibody. If the analyte is present in the fluid sample, it will bind at least a fraction of the labeled anti-analyte antibody. As the fluid sample migrates along the membrane test strip by capillary action, it carries the labeled anti-analyte antibody along until it reaches the test region. The test region contains an immobilized anti-analyte antibody, which may be reactive against a different epitope of the analyte than the labeled anti-analyte antibody. If the analyte is present in the fluid sample, it forms a scaffold through which the labeled antibodies are immobilized in the test region. The fraction of the labeled antibodies captured in the test region is thus determined by the concentration of analyte in the fluid sample. If the analyte of interest is present above a predetermined threshold concentration, a sufficient fraction of the labeled antibodies are captured, resulting in a visible signal in the test region; otherwise, an insufficient fraction of the antibodies are captured and no signal is visible in the test region.

Thus, according to an embodiment of the invention employing a sandwich assay, an analyte-positive fluid specimen will generate a colored line in the test region of the membrane test strip due to the capture of the labeled antibody in the test region, whereas an analyte-negative fluid sample will not generate a fine in the test region due to failure to capture the labeled antibody.

Embodiments of the invention include a positive control to indicate that the assay has functioned properly and is complete. For example, the dye region may include a labeled control protein, including without limitation a labeled control antibody, and the control region of the membrane test strip may contain an immobilized control agent able to capture the labeled control protein, such as an antibody or a control analyte. The control region may be located distal to each test region on the membrane test strip, such that the fluid sample will encounter each test region before encountering the control region. The reaction of the labeled control protein with the immobilized control agent produces a colored line in the control region, indicating that a proper volume of the fluid sample has been added and membrane wicking has occurred, and the assay has worked properly.

An embodiment of the invention concurrently tests for multiple analytes, for example by employing membrane test strips capable of testing multiple analytes concurrently (for example, by containing multiple anti-analyte antibodies in the dye region and having multiple compatible test region), and/or by employing multiple membrane test strips within the same apparatus. An embodiment of the invention includes both membrane test strips that employ a competitive assay and a sandwich assay, for example on different membrane test strips within the device and/or on the same membrane test strip within the device.

Embodiments of the invention may provide quantitative determination of the concentration of an analyte that is present in the fluid sample. For example, the apparatus may include multiple membrane test strips having varying amounts of an anti-analyte antibody, resulting in varying analyte sensitivity, such that the concentration of the analyte is indicated by which of the membrane test strips show or fail to show a colored line in the test region.

Antibodies

An embodiment of the invention employs antibodies for the detection of analytes. The term "antibody" (Ab) as used herein includes monoclonal antibodies, polyclonal antibodies, multispecific antibodies (for example bispecific antibodies), and antibody fragments, so long as they exhibit the desired activity. The term "monoclonal antibody" as used herein refers to an antibody obtained from a population of substantially homogeneous antibodies, that is, the individual antibodies comprising the population are identical except for possible naturally occurring mutations that may be present in minor amounts.

The terms "labeled antibody" and "labeled control protein" refer to an antibody or protein that is conjugated directly or indirectly to a label. The label is a detectable compound or composition that may be detectable by itself, Including without limitation a dye, colloidal metal (including without limitation colloidal gold), radioisotope, or fluorescent compound, or, in the case of an enzymatic label, may catalyze chemical alteration of a substrate compound or composition which is detectable, or any combination of the foregoing.

Analytes According to an embodiment of the invention, the apparatus includes a device for testing a fluid sample for the presence of analytes. The present invention contemplates testing for any analyte. Without limitation, analytes that may be tested for include drugs of abuse or their metabolites, analytes indicating the presence of an infectious agent or product of an infectious agent, allergen, pollutant, toxin, contaminant, analyte with diagnostic or medical value, antibody against any of the foregoing, and any combination thereof.

According to an embodiment of the invention, analytes that may be tested for include drugs of abuse and their metabolites, including without limitation 7-acetaminoclonazepam, alkyl nitrites, alpha-hydroxyalprazolam, alprazolam, 2-amino-2'-chloro-5-nitrobenzophenone, 7-aminoclonazepam, 7-aminonitrazepam, amitriptyline, amobarbital, amoxapine, amphetamine, anabolid steroids, androgen, androstadienone, aprobarbital, atropine, barbiturates, benzodiazepines, benzoylecgonine, benzylpiperazine, boldenone undecylenate, 4-bromo-2,5-dimethoxyphenethylamine, bovine growth hormone, butabarbital, butalbital, butripryline, 4-chlordehydromethyltestosterone, chloroform, clomipramine, clonazepam, clostebol, cocaethylene, cocaine, codeine, codeine-6-glucuronide, cotinine, dehydroepiandrosterone, desipramine, desmethyldiazepam, desoxymethyltestosterone, dexmethylphenidate, dextroamphetamine, dextromethorphan, dextropropoxyphene, dextrorphan, 2,5-diamino-2'-chlorobenzophenone, diamorphine, diazepam, dibenzepin, dihydrotestosterone, dimenhydrinate, 2,5-dimethoxy-4-(n)-propylthiophenethylamine, 2,5-dimethoxy-4-ethylphenethylamine, 2,5-dimethoxy-4-iodophenethylamine, dimethyl ether, dimethyltryptamine, dimethyltryptamine, diphenhydramine hydrochloride, dosulepin hydrochloride, dothiepin hydrochloride, doxepin, drostanolone, ecgonine, ecgonine methyl ester, ephedrine, ergine, estren, 5-estrogen, ethyl-5-(1'-methyl-3'-carboxypropyl)-2-thiobarbituric acid, 5-ethyl-5-(1-'-methyl-3'-hydroxybutyl)-2-thiobarbituric acid, ethylestrenol, ethylphenidate, fentanyl, flunitrazepam, fluoxymesterone, furazabol, gamma-hydroxybutyrate, 1-(beta-D-glucopyranosyl) amobarbital, growth hormone, heroine, hexabarbital, human chorionic gonadotropin, human growth hormone, hydrocodone, hydromorphone, (+)-3-hydroxy-N-methylmorphinan, 3-hydroxy clonazepam, 11-hydroxy-tetrahydrocannabinol (11-hydroxy-THC), 3'-hydroxyamobarbital, p-hydroxyamphetamine, p-hydroxynorophedrine, imipramine, iprindole, kava, katamine, levomethylphenidate, iofepramine, lorazepam, lorazepam-glucuronide, lysergic acid diethylamide, meperidine, mescaline, mestanolone, mesterolone, metachlorophenylpiperazine, methadone, methamphetamine, methandrostenolone, methcathinone, 3,4-methylenedioxyamphetamine, methanolone, methanolone enanthate, methylenedioxymethamphelamine (ecstacy), methylphenidate, methylphenobarbital, methyl testosterone, mibolerone, (+)-3-morphinan, morphine, nandrolone, nicotine, nitrazepam, N-methyl-diethanciamine, norbolethone, norcodeine, norethandrolone, norketamine, nortriptyline, opiates, opipramol, opium, oxabolone opionate, oxandrolone, oxazepam, oxycodone, oxymetholone, oxymorphone, pentobarbital, phencyclidine, phenethylamines, phenobarbital, 4-phenyl-4-(1-piperidinyl)-cyclohexanol, 1-phenyl-1-cyclohexene, phenylacetone, 5-[N-(1-phenylcyclohexyl)]-aminopentanoic acid, 1-(1-phenylcyclohexyl)-4-hydroxypiperidine, piperidine, protriptyline, psilocin, psilocybin, quinbolone, salvinorin A, scopolamine, secobarbital, sodium thiopental, stanozolol, telbutal, temazepam, testosterone, testosterone proprionate, tetrahydrocannabinol (THC), THC-COOH, tetrahydrogestrinone, toluene, trenbolone, tricyclic antidepressant, 3-trifluoromethylphenylpiperazine, trimipramine, tryptamines, or any combination thereof. The minimum concentration level at which the presence of any particular drug or metabolite is detached may be determined by various industry minimum standards, such as, for example, the National Institute on Drug Abuse (NIDA), the Substance Abuse & Mental Health Services Administration (SAMHSA), and the World Health Organization (WHO).

According to an embodiment of the invention, analytes that may be tested for include infectious agent or the products of an infectious agent, including without limitation Acanthamoeba, aflatoxin, alimentary mycotoxlcoses, altertoxin, amoeba, Anisakis, Ascaris lumbricoides, *Bacillus arthracis, Bacillus cereus* or its toxin, bacteria, bovine spongiform encephalopathy priors, *Brucella, Caliciviridae, Calymmatobacterium granulomatis, Campylobacter, Campylobacter jejuni, Candida, Candida albicans, Cephalosporium, Chlamydia trachomatis*, chronic wasting disease prions, Citrinin, *Clostridium botulinum* or its toxin, *Clostridium perfringens, Corynebacterium ulcerans, Coxielia burnetil*, Creutzieldt-Jakob disease prions, Granuloma neoformans, Cryptosporidium, Cryptosporidium parvum Cycloplazonic acid, Cyclospera cayetanensis, Cytochaiasin, Cytomegalovirus, Diphyilobothrium, *Escherichia Coli*, Ebola, endotoxin, Entamceba histolytica, Enterovirus, Ergopeptine alkaloid, Ergot alkaloid, Ergotamine, *Escherichia coli* 0157, Eustrongylides, Fasciola hepatica, fatal familial insomnia prions, flatworm, *Francisella tularensis*, Fumitremorgen B.sub.1 Fumonisin, Fusarium, Fusarochromanone, genital warts, Gerstmann-Straussler-Scheinker syndrome prions, Giardia, Giardia lamblia, Granuloma inguinale, H7 enterohemorrhagic, *Haemophilus ducreyl, Helicobacter pylori*, Hepatitis, Hepatitis A, Hepatitis B, Hepatitis C, Hepatitis D, Hepatitis E, Hepatitis E, herpes simplex virus, Histoplasma capsulatum, HIV, HIV-1, HIV-2, human papillomavirus, influenza, Kaposi's sarcoma-associated herpesvirus, Kojic acid, kuru prions, *Listeria monocytogenes*, Lolitrem alkaloids, marburg virus, Methicillin-resistant *Staphylococcus aureus* or its toxin, molluscum, Moniliformin, mononucleosis, mycobacteria, *Mycobacterium tuberculosis, Mycoplasma, Mycoplasma hominis*, Mycotoxins, Myrothecium, Nanophyetus, *Neisseria gonorrhosae*, nematode, Nivalenol, Norovirus, Oohratoxins, Oosporeine, parasite, Patulin, Paxilline, Penitrem A, Phomopsins, Plasmodium, Platyhelminthes, *Plesiomonas shigelloides,* Pneumococcus, Pneumocystis jirovecii, prions, protozoa, rhinovirus, Rotavirus, *Salmonella,* Sarcocystis hominis, Sarcocystis sulhominis, scraple prions, sexually transmitted disease, *Shigella, Shigella,* Sporidesmin A, Stachybotrys, *Staphylococcus aureus* or its toxin, Sterigmatocystin, *Streptococcus, Streptococcus pneumoniae, Streptococcus pyogenes,* Taenia saginata, Taenia solium, tapeworm, Tenia solium, Tinea, Toxoplasma gondii, Tremorgenic mycotoxins, Treponema palidum, Trichinella spiralis, Trichoderma, Trichomonas vaginalis, Trichothecene, Trichuris trichlura, Typanosoma cruzi, *Ureaplasma urealyticum,* Verrucosidin, Varruculogen, *Vibrio cholerae* non-01, *Vibrio cholerae* 01, *Vibrio-parahaemolyticus, Vibrio vulnificus,* viruses, yeast infections, *Yersinia enterocolitica, Yersinia pseudotuberculosis,* Zearalenois, Zearalenone, antibodies against any of the foregoing, or any combination thereof.

According to an embodiment of the invention, the analytes to be tested for include allergens, including without limitation aesculus, aider, almonds, animal products, arternisia vulgaris, beans, bet sting venom, birch, calyx, cat dander, celeriac, celery, *Chenopodium album,* cockroach, corn, dander, dong dander, drugs, dust mite excretion, egg albumen, eggs, Fei d 1 protein, fruit, fur, grass, hazel, hornbeam, insect stings, latex, legumes, local anaesthetics, maize, metal, milk, mold spores, mosquito saliva, mouse dander, nettle, olea, peanuts, peas, pecans, penicillin, Plant pollens, plantago, platanus, poplar, pumpkin, ragweed, rat dander, ryegrass, salicylates, seafood, sesame, sorrel, soy, soybeans, sulfonamides, tilia, timothy-grass, tree nuts, trees, wasp sting venom, weeds, wheat, willow, antibodies against any of the foregoing, or any combination thereof.

According to an embodiment of the invention, the analytes to be tested for include pollutants, toxins, and contaminants, including without limitation 1,2-Dibromoethane, acrylamide, aldehydes, arsenic, artificial growth hormone, asbestos, benzene, benzopyrene, carcinogens, dichloro-diphenyl-trichloroethane, formaldehyde, kepone, lead, mercury, methylmercury, nitrosamines, N-nitroso-N-methyl-urea, organochlorine insecticides, pesticides, polychlorinated biphenyls, polychlorinated dibenzofurans, polychlorinated dibenzo-p-dloxins, recombinant bovine growth hormone, recombinant bovine somatotropin, toluene, vinyl chloride, antibodies against any of the foregoing, or any combination thereof.

According to an embodiment of the invention, the analytes to be tested for include analytes with diagnostic or medical value, including without limitation acid phosphatase, active-B12, AFP, Alanine Aminotransferase, Alanine Aminotransferase, Albumin, Albumin BCG, Albumin BCP, Alkaline Phosphatase, Alpha-1 Antitrypsin, Alpha-1 Glycoprotein, Amikacin, Ammonia, Amylase, Anti-CCP, Anti-Tg, Anti-TPO, Apolipoprotein A1, Apolipoprotein B, ASO, Asparate Aminotransferase, Aspartate Aminotransferase, B12, Beta2 Microglobulin, Beta2 Microglobulin, BNP, CA 125, CA 125 II, CA 15-3, CA 19-9 XR, Calcium, Carbamazepine, Carbon Dioxide, CEA, Ceruloplasmin, Cholesterol, CK-MB, Complement C3, Complement C4, Cortisol, C-Peptide, C-Reactive Protein, Creatine Kinase, Creatinine, CRP Vario, Cyclosporine, Cyclosporine and Metabolite-Whole Blood, Cyclosporine Monoclonal-Whole Blood, D-Dimer, DHEA-S, Digitoxin, Digoxin, Digoxin, Digoxin II, Digoxin III, Direct Billirubin, Direct LDL, Estradiol, Ferritin, FLM II, Folate, Free Carbamazepine, Free Phenytoin, Free PSA, Free T3, Free T4, Free Valproic acid, FSH, Gamma-Glutamyl Transferase, Gentamicin, Glucose, Glycated Hemoglobin, Haptoglobin, hCG, Hemoglobin, Homocysteine, ICT CI-, IGFBP-1, Immunoglobulin, Immunoglobulin A, Immunoglobulin E, immunoglobulin G, Immunoglobulin M, Insulin, Intact PTH, Iron, K+, Kappa Light Chain, Lactate Dehyrogenase, Lactic acid, Lambda Light Chain, LH, Lidocaine, Lipase, Lithium, Lp, magnesium, metabolites, Methotrexate II, Microalbumin, MPO, Myoglobin, Na+, N-Acetyl-procainamide, neonatal Billirubin, NGAL, P-Amylase, Pepsinogen I, Pepsinogen II, Phenobarbital, Phenytoin, Phosphorus, Prealbumin Procainamide, Progesterone, Prolactin, Quinidine, Rheumatoid Factor, SHBG, Sirollmus, STAT CK-MB, T4, Tacrolimus, Tacrolimus II, Testosterone, Tg, Theophylline, Theophylline II, TIBC, TIMP-1, Tobramycin, Total Billirubin, Total Estriol, Total Protein, Total PSA, Total T3, Total T4, Transferrin, Triglycerides, Troponin-I, Troponin-I ADV, TSH, T-Uptake, UIBC, Ultra HDL, Urea Nitrogen, Uric Acid, Urine/CSF Protein, Valproic Acid, Vancomycin, Vancomycin II, Vitamin D, antibodies against any of the foregoing, or any combination thereof.

Receiving Member

According to an embodiment or the invention, the apparatus includes a receiving member, having an opening to receive a fluid sample, For example, the receiving member may be dimensioned to receive a fluid collector. In an embodiment of the invention, the receiving member may be in fluid communication with other components of the apparatus, for example at least one membrane test strip, sample retention member, and/or an Immunoassay-based fingerprint acquisition pad, through channels, for example tubes, piping, channels molded or carved into the apparatus, or any other suitable structure, made of any suitable material, for example plastic, ceramic, metal, glass, wood, rubber, polymer, fiber-reinforced polymer, or any combination thereof.

According to an embodiment of the invention, the channel or channels providing fluid communication between the components may have differing flow resistance, for example having channels, channel segments, or openings, that are narrower, wider, longer, or shorter than others, and/or having fluid paths with varying amounts of vertical rise or drop, such that the fluid channels within the device have varying degrees of flow resistance. For example, the channel that provides the fluid communication of the sample receiving member with the at least one membrane test strip may have greater flow resistance than the at least one channel that provides the fluid communication of the sample receiving member with the sample retention member, to ensure that a portion of the fluid sample is collected in the sample retention member.

In an embodiment of the invention, a single channel having multiple openings may connect the receiving member to each of the components of the apparatus with which it is in fluid communication, for example the at least one membrane test strip, sample retention member, and/or immunoassay-based fingerprint acquisition pad.

In an embodiment of the invention, the receiving member may include two or more chambers for receipt of a multi-pronged fluid collector, including but not limited to a dual-swab fluid collector. Components of the apparatus may be solely connected to one of the multiple chambers. For example, in a two chamber embodiment, one chamber may be solely connected to a sample retention member to ensure that a portion of the fluid sample is collected and stored without interaction of the other components of the apparatus.

An embodiment of the invention may accommodate fluids of varying viscosity, for example water, saliva, urine, blood, and liquids associated with genomics and proteomics. Generally, this is accomplished by varying the diameter of the channel or channels that provide the fluid communication of the sample receiving member with the other components of the apparatus, for example providing a wider channel diameter to accommodate a more viscous fluid.

In an embodiment of the invention, a channel dimensioned to be compatible with a fluid having the viscosity of water provides the fluid communication of the sample receiving member with the at least one membrane test strip and at least one channel dimensioned to be compatible with a fluid having the viscosity of water provides the fluid communication of the sample receiving member with the sample retention member.

In an embodiment of the invention, a channel dimensioned to be compatible with a fluid having the viscosity of urine provides the fluid communication of the sample receiving member with the at least one membrane test strip and at least one channel dimensioned to be compatible with a fluid having the viscosity of urine provides the fluid communication of the sample receiving member with the sample retention member.

In an embodiment of the invention, a channel dimensioned to be compatible with a fluid having the viscosity of saliva provides the fluid communication of the sample receiving member with the at least one membrane test strip and at least one channel dimensioned to be compatible with a fluid having the viscosity of saliva provides the fluid communication of the sample receiving member with the sample retention member.

In an embodiment of the invention, a channel dimensioned to be compatible with a fluid having the viscosity of blood provides the fluid communication of the sample receiving member with the at least one membrane test strip and at least one channel dimensioned to be compatible with a fluid having the viscosity of blood provides the fluid communication of the sample receiving member with the sample retention member. In an embodiment of the invention, a channel dimensioned to be compatible with a fluid having the viscosity of mucus provides the fluid communication of the sample receiving member with the at least one membrane test strip and at least one channel dimensioned to be compatible with a fluid having the viscosity of mucus provides the fluid communication of the sample receiving member with the sample retention member.

In an embodiment of the invention, a channel dimensioned to be compatible with a fluid having the viscosity of liquid associated with cell separation provides the fluid communication of the sample receiving member with the at least one membrane test strip and at least one channel dimensioned to be compatible with a fluid having the viscosity of liquid associated with cell separation provides the fluid communication of the sample receiving member with the sample retention member.

In an embodiment of the invention, a channel dimensioned to be compatible with a fluid having the viscosity of liquid biopsy, such as proteomics or genomics, provides the fluid communication of the sample receiving member with the at least one membrane test strip and at least one channel dimensioned to be compatible with a fluid having the viscosity of liquid biopsy provides the fluid communication of the sample receiving member with the sample retention member. Proteomics is the study of proteins. Genomics is a branch of molecular biology concerned with the structure, function, evolution, and mapping of genomes.

In an embodiment of the invention, the receiving member may have an inner surface, for example a lower surface, that an absorbent material, such as an absorbent material present in a fluid collector, may be compressed against, thereby expelling the fluid sample from the absorbent material. For example, the absorbent material may be compressed directly between a compression member present on the fluid collector and the lower surface of the receiving member or the receiving member may provide structural support to facilitate compression of the absorbent material between a compression member and the housing that at least partially surrounds the absorbent material.

Sample Retention Member

According to an embodiment of the invention, the apparatus includes a sample retention member. The sample retention member may be used to securely contain a portion of the fluid sample, such as a split sample. The retained portion of the fluid sample may be used for further testing, for example for confirmation of a test result obtained using a membrane test strip, or to test for the presence or absence of other analytes in the fluid sample. The retained portion of the fluid sample may also be used for confirmation of the test subject's identity through analysis of a distinguishing feature thereof, including without limitation DNA, cells, proteomics, metals, and liquid biopsy.

According to one embodiment of the invention, the sample retention member includes an absorbent material, for example a pad or sponge, or made of woven or non-woven fibrous or fabric-like material, for example cellulose or a cellulose derivative, cotton, hydrophilic foam, wood pulp, polyvinyl alcohol fibers, or any combination thereof. The sample retention member may include an absorbent material that is part of the sample collection apparatus. The absorbent material may be surrounded by a barrier, such as a liquid-impermeable material, including without limitation plastic, ceramic, metal, glass, wood, rubber, polymer, fiber-reinforced polymer, or any combination thereof, to prevent the retained sample from leaking or evaporating. In an embodiment of the invention, the absorbent material may be removably attached to the apparatus to facilitate retrieval of the retained fluid sample. In an embodiment of the invention, the absorbent material may be accessed using a needle, for example by piercing a barrier surrounding the absorbent material. The retained sample may then be removed, for example, into a syringe attached to a needle, by means of withdrawal of the syringe to create suction.

According to an embodiment of the invention, the sample retention member includes a storage container defining a volume for storage of the fluid sample. In one embodiment of the invention, the sample retention member may be a vial made from a breakable or nearly unbreakable material, including without limitation glass, plastic, ceramic, metal, metal foil, wood, rubber, polymer, fiber-reinforced polymer, or any combination thereof. In an embodiment of the invention, the storage container may be accessed using a needle to pierce the wall of the storage container. For example, the storage container may include a pierceable member, such as a region of decreased wall thickness, and/or made of a soft, pierceable, or breakable material, including without limitation plastic, ceramic, metal, glass, metal foil, wood, rubber, polymer, fiber-reinforced polymer, or any combination thereof, that may be pierced. The retained sample may then be removed, for example, into a syringe attached to a needle, by means of withdrawal of the syringe to create suction. In an embodiment of the invention, the storage container may be removably attached to the apparatus, including without limitation, through a line of weakness that may allow the storage container to be broken free form the apparatus, through a threaded connection mechanism between the sample retention member and the fluid sample testing device, or through a twisting lock connection mechanism between the sample retention member and the fluid sample testing device.

According to an embodiment of the invention, the removable sample retention member may be linked to or coded consistently with the fluid sample testing device, including but not limited to, identical or related identification or serial numbers on both the sample retention member and the fluid sample testing device, identical or related bar code information on both the sample retention member and the fluid sample testing device, and the inclusion of radio frequency identification devices (RFID) on the sample retention member or the sample retention member and the fluid sample testing device. RFID incorporates the use of electromagnetic or electrostatic coupling in the radio frequency (RF) portion of the electromagnetic spectrum uniquely identify an object; such unique identification information may be information specific to the sample provider or information unique to the fluid sample testing device.

According to an embodiment of the invention, the sample retention member contains substances that facilitate a further use of the sample, including without limitation preservatives of stabilizers able to preserve sample integrity, for example substances able to inhibit microbial growth, kill microbes, prevent sample leakage, prevent sample evaporation, inhibit chemical or enzymatic degradation of substances in the sample, support survival of cells or other microbes in the sample, or any combination thereof.

According to an embodiment of the invention, the sample retention member may be bonded to a fingerprint acquisition pad. For example, such a bond may provide a safeguard against dissociation of the retained sample from the fingerprint.

According to an embodiment of the invention, the sample retention member may be in fluid contact solely with the sample receiving member and may not have any fluid contact with any other component of the apparatus.

The retained fluid sample may be used for further confirmation testing, including without limitation gas chromatography, liquid chromatography, mass spectrometry, liquid or gas chromatography with tandem mass spectrometry, polymerase chain reaction, DNA sequencing, Enzyme-Linked ImmunoSorbent Assay, Western Blotting, culturing for growth, or any combination thereof, using the retained fluid sample.

Fluid Collector

In embodiment of the apparatus comprises a fluid collector for collecting a fluid sample. The present invention contemplates collecting a sample from a specific subject, such as a human subject, or testing environmental samples, such as testing air, water, soil, or some other substance, or a food or beverage, or a liquid extract of any of the foregoing for example, without limitation. The fluid collector is operative associated with the apparatus. The fluid collector may be removably associated with the apparatus/affixed to the apparatus, or comprise multiple units of which one or more is affixed or removably associated with the apparatus.

In an embodiment of the invention, the fluid collector includes an absorbent material or swab capable of absorbing a desired quantity of a fluid sample. The absorbent material may be made of any suitable material known to a person in the art, for example, without limitation, a pad or sponge, or woven or non-woven fibrous or fabric-like material, including without limitation cellulose or a cellulose derivative, cotton, hydrophilic foam, wood pulp, polyvinyl alcohol fibers, or any combination thereof. In an embodiment of the invention, the fluid collector includes a compression member, able to compress the absorbent material, that may be used to expel air from the absorbent material prior to collection of the fluid sample and/or encourage the fluid sample to flow into the absorbent material by creating suction as the compressed absorbent material returns to the uncompressed state. A compression member may also be used, for example, to compress the absorbent material and expel a fluid sample contained therein.

In one embodiment of the invention, the fluid collector includes multiple collection swabs. For example, a two-prong fluid collector with dual swabs may be implemented to collect the sample. In one embodiment, each swab of a multi-swab fluid collector may be selected based upon the specific swab collection characteristics. For example, in a dual-swab fluid collector, each swab may contain a material to assist in the collection of different samples such as the collection of different cell material.

A sufficiency indicator on the collector is contemplated. For example without limitation, a color indicator may either appear or disappear when a sufficient sample has been collected, for example when a sufficient volume has been absorbed to reach the location in the absorbent material where the sufficiency indicator is disposed. According to an embodiment of the invention, the sufficiency indicator may be operatively associated with the absorbent material and may protected from direct contact with the source of the fluid sample by a barrier, such as a transparent barrier, for example plastic or glass, such that the fluid sample will only reach the sufficiency indicator by passing into the absorbent material.

The sufficiency indicator color may be in the shape of a word or symbol that appears or disappears when a sufficient sample has been collected. For example, the sufficiency indicator may a diffusible dye, wherein dilution of the dye by the fluid sample causes a color to disappear, indicating that a sample of sufficient volume has been collected. In an embodiment of the invention, a combination of a non-diffusible and diffusible dye may be used together, such that the non-diffusible dye remains and provides an informative message when the diffusible dye disappears, for example the diffusible dye may form the letters "in" in the word "insufficient" such that the non-diffusible dye remains and forms the word "sufficient" when a sufficient sample has been collected.

The sufficiency indicator may be a pH-sensitive substance that changes color when the sample is encountered. For example, multiple pH sensitive indicators responding to different pH values may be preset, such that a color change is observed whether the sample is acidic, basic, or neutral. According to an embodiment of the invention, a pH-changing substance, such as an acid or base, may be disposed within the absorbent material, such that the sample will be of the correct pH to elicit the desired color change in the sufficiency indicator.

A closure member may be used. The closure member is capable of sealing the open end of a sample receiving member when the fluid collector is inserted into the open end of a sample receiving member. For example, the closure member may be dimensioned to fit closely in the opening in the open end of the receiving member, and the closure member or the open end of the receiving member may include a compressible material, including without limitation natural rubber such as vulcanized rubber, synthetic rubber such as neoprene or nitrite rubber, plastic, ceramic, or any combination thereof, disposed at the interface between the closure member and the opening in the open end of the sample receiving member, capable of creating a seal, such as an airtight or a watertight seal, when the sample receiving member receives the fluid collector.

After the fluid collector has been inserted into the sample receiving member, a device for securing the fluid collector within the sample receiving member is contemplated. The means for securing may prevent removal of the fluid collector from the sample receiving member after it has been inserted therein. The means for securing the fluid collector within the sample receiving member may include at least one projection extending from the fluid collector that cooperates with the at least one projection located on the inner surface of the sample receiving member, where such projections may include for example at least one locking tab and/or at least one annular ring. According to an embodiment of the invention, a closure member on the fluid collector may form a sufficiently secure closure as to constitute means for securing the fluid collector within the sample receiving member.

The sample receiving member may also include a tamper-evident seal, such that attempting to tamper with the contents of the apparatus will result in a visual indicator, for example by tears or breakage visible in an imprinted seal, for example tape or adhesive-backed foil having characters, symbols or a signature on a surface. Such a tamper-evident seal may be placed on the apparatus before its use, to create a visual confirmation that the intents of the apparatus have not been altered via the open end of the receiving member prior to testing, or after its use, to create a visual confirmation that the contents of the apparatus have not been altered via the open end of the receiving member subsequent to testing. According to an embodiment of the invention, the means for securing the fluid collector within the sample receiving member may constitute a tamper evident seal, in that attempted removal of the fluid collector from the sample receiving member after it has been inserted therein may result in visible damage to the apparatus.

According to an embodiment of the invention, the fluid collector includes a handle, for example made of wood, plastic, ceramic, or metal, and disposed, for example, at the end distal to the absorbent material. The handle may be removably attached, for example through an interference fit, adhesive, glue, or epoxy, that breaks or separates when the handle is twisted and/or pulled, or by a structure that allows the handle to be broken away, for example, a line of weakness.

The fluid collector may include a housing that at least partially surrounds the absorbent material. The housing may have multiple openings to allow the fluid sample to be absorbed by and expressed from the absorbent material. The openings in the housing may contain filtration members able to strain particulates from the fluid sample, resulting in reduction of the number of particulates that enter the absorbent material. The fluid collector may include a compression member able to compress the absorbent material against the housing. For example, the housing may be slideably coupled to a compression member with the absorbent material disposed between the compression member and an inner surface of the housing, such that the absorbent material may be compressed by movement of the compression member towards an inner surface of the housing. An embodiment of the invention includes means for securing the absorbent material in the compressed state, including without limitation cooperating threads, projections, and/or grooves operatively associated with the compression member and the housing. The absorbent material may be released from the compressed state before, concurrently with, or after encounter with the fluid sample, facilitating entry of the fluid sample into the absorbent material as the absorbent material returns to the relaxed state, creating suction. For example, the absorbent material may be operatively associated with a spring, such that compression of the absorbent material results in compression of the spring, and when compression is released the spring assists return of the absorbent material to the uncompressed state.

In an embodiment of the invention, the fluid collector is operatively associated with the lid of a fluid container including without limitation a urine cup. For example, the absorbent material may be disposed on the inner side of the lid, such that attachment of the lid to the fluid container results in contact between the absorbent material and a fluid sample. In certain embodiments of the invention, a portion of the fluid collector including the lid may be removably associated with a portion of the fluid collector including the absorbent material, allowing the absorbent material to be separated from the lid. The operative association of the fluid collector with the lid may include means for arresting the rotation of part of the fluid collector relative to the lid, including without limitation cooperating projections present on one member and grooves or slots present on the other member, for example to facilitate release of means by which the absorbent material is fixed in the compressed state.

Saliva Producing Substances

Use of a saliva producing substance is contemplated by the present invention. Saliva producing substances elicit or increase saliva production in the test subject. For example, without limitation, the saliva producing substance may sugars, salts, acids, or any combination thereof. In an embodiment of the invention, the saliva producing substance may be associated with a fluid collector, for example located on or in the absorbent material or the housing. In an embodiment of the invention, the saliva producing substance may be separated from the fluid collector, for example in the form of a gum, candy, or powder, for administration to the test subject before, during or after the fluid collector is inserted into the test subject's mouth.

For example, without limitation, the sugar may be a monosaccharide, a disaccharide, a trisaccharide, an oligosaccharide, a polysaccharide, acarbose, allose, altrose, amylose, arabinose, calibiose, cyclodextrin, alpha-cyclodextrin, beta-cyclodextrin, gamma-cyclodextrin, deoxyglucose, dextrin, dihydroxyacetone, erythrose, erythrulose, ficoli, fructo-oligosaccharides, fructose, galacto-oligosaccharides, galactose, gentiobiose, glucoasmine, glucose, glyceraldehyde, glycogen, gulosse, idose, inositol, inulin, isomaltose, lactose, lyxose, maltose, maltosyl-cyclodextrin, malt-trifose, mannan-oligosaccharides, mannoheptulose, marinose, melexltose, monnitol, psiccae, raffinose, ribitol, ribose, ribulose, sedoheptulose, sorbitol, sorbose, sucrose, tagatose, talose, threose, trehalose, xylose, xylulose, or any combination thereof.

For example, without limitation, the salt may an inorganic salt, organic salt, acid salt, alkali salt, neutral salt, or amino acid salt, or any combination thereof. The salt may include a cation and an anion, for example without limitation thereto, the cation may be aluminum, ammonium, barium, beryilium, calcium, cesium, chromium(II), chromium(III), chromium(IV), cobalt(II), cobalt(III), copper(I), copper(II), copper(III), gallium, helium, hydrogen, hydronium, iron(II), iron(III), lead(II), lead(IV), lithium, magnesium, manganese (II), manganese(III), manganese(IV), manganese(VII), nickel(II), nickel(III), nitronium, potassium, pyridinium, silver, sodium, strontium, tin(II), tin(IV), zinc, or any combination thereof, and an anion may be acetate, amide, tartrate, borate, bromate, bomide, carbonate, chlorate, chloride, chlorile, chromate, citrate, cyanate, dichormate, dihydrogen phosphate, fluide, formate, glutamate, hydride, hydrogen carbonate, hydrogen oxalate, hydrogen phosphate, hydrogen sulfate, hydrogen sulfite, hydroxide, hypobromite, hypochlorite, lodate, iodide, nitrate, nitride, nitrite, oxalate, oxide, perchlorate, permanganate, peroxide, phosphate, phosphide, phosphite, pyrophosphate, sulfate, sulfide, sulfite, telluride, thiocyanate, thiosulfate, or any combination thereof. For example, according to an embodiment of the invention, the salt may be sodium chloride or potassium chloride.

The acid may be any suitable acid known to a person skilled in the art, for example acetic acid, acrylic acid, adipic acid, alginic acid, alkanesulfonic acid, amino acid, asorbic acid, benzoic acid, boric acid, butyric acid, carbonic acid, carboxylic acid, citrio acid, fattys acid, folic acid, formic acid, fumaric acid, gluconic acid, hdyriodic acid, hydrobromic acid, hydrochloric acid, hydroquinosulfonic acid, isoascorbic acid, lactic acid, maleic acid, malio acid, malonic acid, methanesulfonic acid, nitric acid, oxalic acid, p-toluenesulfonic acid, para-bromophenylsulfonic acid, phosphoric acid, propionic acid, salicyclic acid, stearic acid, succinic acid, sulfuric acid, tannic acid, tartaric acid, thioglycolic acid, toluenesulfonic acid, uric acid, or any combination thereof.

Fingerprint Identification

An embodiment of the present invention includes a fingerprint pad to provide identification of an individual associated with the test, such as the test subject, test administrator, and/or one or more witnesses. The fingerprint pad may employ any suitable fingerprinting methodology, for example, without limitation, ink-based, immunoassay-based, electronic, semi-inkless, or inkless. In an embodiment of the invention, the fingerprint pad may be able to collect multiple fingerprints, for example having multiple fingerprint pads, having one fingerprint pad of sufficient size to accommodate multiple fingerprints, or having an electronic fingerprint pad.

The fingerprint pad may be an ink-based fingerprint pad. An embodiment of the invention includes a dispenser able to dispense an ink that can elicit a signal in the ink-based fingerprint pad. The fingerprint pad may also be inkless or semi-inkless, for example requiring no ink or compatible with an activator that appears transparent on the subject's skin, is readily cleaned off the subject's skin, or readily disappears, for example, when the subject's hands are rubbed together. According to an embodiment of the invention, the inkless fingerprint pad may be immunoassay-based, for example as described within U.S. Pat. No. 6,352,863 to Raouf A. Guirguis, issued Mar. 5, 2002 (the "'863 patent"), and U.S. Pat. No. 5,244,815 to Raouf A. Guirguis, issued Sep. 14, 1993 (the "'815 patent"), which are incorporated herein by reference in their entirety. The immunoassay-based fingerprint pad may or may not be in fluid communication with a sample receiving member. Other embodiments of the invention may incorporate various features of the embodiments disclosed within the '863 and '815 patents. In embodiment of the invention having an inkless or semi-inkless fingerprint pad that requires an activator to elicit a signal, the apparatus may also include a dispenser to dispense the activator. According to an embodiment of the invention, the fingerprint pad may have a surface, such as an absorbent or adhesive surface, able to gather sweat, oils, and/or skin cells when a finger is pressed against it, that may require further processing to permit clear visualization of the fingerprint.

According to an embodiment of the invention, an inkless fingerprint pad may be an electronic fingerprint pad, including without limitation an optical scan fingerprint reader or a solid-state fingerprint reader. An embodiment of the invention includes a memory element, including without limitation volatile or non-volatile memory, for example a hard disk, floppy disk, magnetic tape, optical disk, flash memory, holographic memory, EEPROM, RAM, DRAM, SDRAM, or SRAM coupled to the fingerprint pad for storage of one or more fingerprints. According to an embodiment of the invention, the electronic fingerprint pads may have electrically charged surface elements, wherein portions of the surface are electrically discharged upon contact with the finger surface, such as the ridges of the finger surface, such that the fingerprint is recorded in the pattern of discharged elements, whereby the fingerprint pattern may be stably stored within the surface for a time after it is created until it is read, for example through connection of the apparatus with an external device, including without limitation a base station. An embodiment of the invention include means of transmission of the captured fingerprint, for example to an external device or network, including without limitation through a hard-wired connection, for example employing wires, cables, or a docking station or docking connector, for employing a connection including without limitation USB, IEEE 1394, serial, parallel, or SCSI, or a wireless connection, for example employing infrared, RF, IEEE 802.11, Bluetooth, IEEE 802.15, or Wi-Fi.

In an embodiment of the invention, a cover encloses the fingerprint acquisition pad. The cover may be secured using various mechanisms, for example, without limitation, a tab-and-slot connector, latch, spring latch, adhesive tape, or security tape. The cover may be secured prior to fingerprint acquisition and/or after fingerprint acquisition.

Although the invention is described herein with reference to specific embodiments, various modifications and changes can be made without departing from the scope of the invention as set forth in the claims below. The combination of embodiments is expressly anticipated, unless the embodiments and specifically mutually exclusive. A claimed invention may include multiple embodiments as disclosed herein. Accordingly, the specification and figures are to be regarded in an illustrative rather than a restrictive sense, and all such modifications are intended to be included within the scope of the invention. Any benefits, advantages, or solutions to problems that are described herein with regard to specific embodiments are not intended to be construed as a critical, required, or essential feature or element of any or all the claims.

From time-to-time, the invention is described herein in terms of these example embodiments. Description in terms of these embodiments is provided to allow the various features and embodiments of the invention to be portrayed in the context of an exemplary application. After reading this description, it will become apparent to one of ordinary skill in the art how the invention can be implemented in different and alternative environments. Unless defined otherwise, all technical and scientific terms used herein have the same meaning as is commonly understood by one of ordinary skill in the art to which this invention belongs.

The preceding discussion is presented to enable a person skilled in the art to make and use the invention. The general principles described herein may be applied to embodiments and applications other than those detailed below without departing from the spirit and scope of the invention as defined by the appended claims. The invention is not intended to be limited to the embodiments shown, but is to be accorded the widest scope consistent with the principles and features disclosed herein.

In addition, while a particular feature of the invention may have been disclosed with respect to only one of several embodiments, such feature may be combined with one or more other features of the other embodiments as may be desired. It is therefore, contemplated that the claims will cover any such modifications or embodiments that fall within the true scope of the invention.

The various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the invention. In addition, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more", "at least", "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Unless stated otherwise, terms such as "first" and "second" are used to arbitrarily distinguish between the elements such terms describe. Thus, these terms are not necessarily intended to indicate temporal or other prioritization of such elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the field or any related fields are intended to be within the scope of the following claims.

One skilled in the art will recognize that different embodiments may be formed in a similar manner having different characteristics depending upon need, performance, or some other criteria. It will thus be appreciated by those skilled in the art that changes could be made to the embodiments described above without departing from the broad inventive concept thereof. It is understood, therefore, that the invention disclosed herein is not limited to the particular embodiments disclosed, but it is intended to cover modifications within the spirit and scope of the present invention as defined by the appended claims.

Although this invention has been described in conjunction with specific embodiments thereof, many alternatives, modifications and variations will be apparent to those skilled in the art. Accordingly, the embodiments of the invention as set forth herein are intended to be illustrative, not limiting. Various changes may be made without departing from the true spirit and full scope of the invention as set forth herein.

Although the invention has been described in conjunction with specific preferred and other embodiments, it is evident that many substitutions, alternatives and variations will be apparent to those skilled in the art in light of the foregoing description. Accordingly, the invention is intended to embrace all of the alternatives and variations that fall within the spirit and scope of the appended claims. For example, it should be understood that, in accordance with the various alternative embodiments described herein, various systems, and uses and methods based on such systems, may be obtained. The various refinements and alternative and additional features also described may be combined to provide additional advantageous combinations and the like in accordance with the present invention. Also as will be understood by those skilled in the art based on the foregoing description, various aspects of the preferred embodiments may be used in various subcombinations to achieve at least certain of the benefits and attributes described herein, and such subcombinations also are within the scope of the present invention. All such refinements, enhancements and further uses of the present invention are within the scope of the present invention.

What is claimed is:

1. A fluid sample testing apparatus comprising:
a housing with a fluid collector tube;
a sample holding container in fluid communication with the fluid collector tube and removably secured to the fluid collector tube;
a fluid collector, wherein the fluid collector has an elongated stem and is adapted for insertion into the fluid collector tube and upon insertion and penetration into the fluid collector tube pressure is generated to release fluid from the fluid collector into the sample holding container;
a gasket positioned in the fluid collector tube having an upper portion engaging a wall of the fluid collector tube and a lower portion of smaller diameter than the upper portion extending into an opening of the sample holding container, wherein the gasket is positioned at an upper location in the fluid collector tube upon insertion of the fluid collector into the fluid collector tube, wherein the gasket is positioned at a lower location in the fluid collector tube after insertion of the fluid collector into the fluid collector tube and at the lower location a surface of the gasket that is positioned between the upper portion and the lower portion engages a top surface of the sample holding container and forms a seal with the sample holding container, wherein air passes outside of the apparatus from the fluid collector tube around an upper portion of the sample holding container before the gasket is positioned at the lower location.

2. The apparatus of claim 1, wherein the fluid collector has an upper sealing portion such that upon substantially complete insertion and penetration of the fluid collector into the fluid collector tube the upper sealing portion seals the fluid collector tube.

3. The apparatus of claim 2, wherein the fluid collector has a lower sealing portion adapted to form a sliding seal between the lower sealing portion and a surface wall of the fluid collector tube as the fluid collector is inserted and penetrated into the fluid collector tube.

4. The apparatus of claim 3, wherein the upper sealing portion forms a stopper seal with an upper surface wall of the fluid collector tube, and the lower sealing portion forms a syringe plunger seal between the lower sealing portion and a lower surface wall of the fluid collector tube.

5. The apparatus of claim 4, wherein the lower sealing portion is formed to have a plurality of spaced apart o-ring portions to form the syringe plunger seal.

6. The apparatus of claim 4, wherein the lower sealing portion is formed to have a textured surface to form the syringe plunger seal.

7. The apparatus of claim 1, wherein the fluid collector includes a swab material at a lower end and a top cap, with the elongated stem extending from proximate to the swab material to proximate to the top cap, wherein the stem has an open cavity containing at least a moisture indication strip that contacts a portion of the swab material and changes color subsequent to contacting fluid absorbed by the swab material.

8. The apparatus of claim 7, wherein the open cavity of the stem further contains a strip indicating the presence or absence of an analyte or pathogen.

9. The apparatus of claim 7, wherein the open cavity of the stem also contains at least one analyte or pathogen detection strip that also is in contact with the swab material, wherein the at least one analyte or pathogen detection strip indicates the presence or absence of an analyte or pathogen.

10. The apparatus of claim 1, wherein the fluid collector includes a swab material at a lower end and a top cap, with the elongated stem extending from proximate to the swab material to proximate to the top cap, wherein the stem has an open cavity containing one or more analyte or pathogen detection strips that are in contact with the swab material, wherein the one or more strips indicate the presence or absence of an analyte or pathogen.

11. The apparatus of claim 10, wherein the open cavity of the stem contains two analyte or pathogen detection strips that are in contact with the swab material and that are arranged in a back-to-back configuration, wherein each of the two strips indicates the presence or absence of one of a first and a second analyte or pathogen.

12. The apparatus of claim 1, wherein a vent path is formed between an attachment portion of the fluid collector tube and the sample holding container, wherein air passes outside of the apparatus from the fluid collector tube around the upper portion of the sample holding container through the vent path before the gasket is positioned at the lower location.

13. The apparatus of claim 12, wherein the attachment portion of the fluid collector tube comprises threads, wherein the sample holding container is removably secured to the fluid collector tube via the threads.

14. The apparatus of claim 1, wherein the sample holding container contains a buffer for transporting a sample contained in the sample holding container to a laboratory.

15. The apparatus of claim 14, wherein the buffer comprises a lysis buffer.

16. The apparatus of claim 14, wherein the buffer comprises an RNA or DNA preservative buffer.

* * * * *